United States Patent
Martinez Ferreira et al.

(10) Patent No.: US 10,820,871 B1
(45) Date of Patent: Nov. 3, 2020

(54) MOBILE X-RAY IMAGING SYSTEM INCLUDING A PARALLEL ROBOTIC STRUCTURE

(71) Applicants: GE PRECISION HEALTHCARE LLC, Wauwatosa, WI (US); IRT JULES VERNE, Bougenais (FR)

(72) Inventors: Carlos Martinez Ferreira, Paris (FR); Adolfo Suarez Roos, Paris (FR); Stephane Felix Caro, Nantes (FR); Damien Charles Chablat, La Chapelle sur Erdre (FR)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 0 days.

(21) Appl. No.: 16/536,947

(22) Filed: Aug. 9, 2019

(51) Int. Cl.
*H05G 1/02* (2006.01)
*A61B 6/00* (2006.01)

(52) U.S. Cl.
CPC .......... *A61B 6/4458* (2013.01); *A61B 6/4405* (2013.01); *A61B 6/4452* (2013.01); *A61B 6/4488* (2013.01); *A61B 6/587* (2013.01)

(58) Field of Classification Search
CPC ......... A61B 6/035; A61B 6/04; A61B 6/4007; A61B 6/4085; A61B 6/4266; A61B 6/4275; A61B 6/4405; A61B 6/4458; A61B 6/4476; A61B 6/501; A61B 6/4447; A61B 6/032; A61B 6/4435
See application file for complete search history.

(56) References Cited

U.S. PATENT DOCUMENTS

| | | | |
|---|---|---|---|
| 4,209,706 A | 6/1980 | Nunan | |
| 6,461,039 B1 | 10/2002 | Klotz et al. | |
| 6,869,217 B2 | 3/2005 | Rasche et al. | |
| 7,008,373 B2 | 3/2006 | Stoianovici et al. | |
| 7,299,806 B2 | 11/2007 | Lokhandwalla et al. | |
| 7,477,722 B2 | 1/2009 | Carrano et al. | |
| 7,620,144 B2 | 11/2009 | Bodduluri | |
| 7,630,751 B2 | 12/2009 | Boese et al. | |
| 7,748,900 B2 | 7/2010 | Maschke | |
| 7,801,342 B2 | 9/2010 | Boese et al. | |
| 7,847,275 B2 | 12/2010 | Marash et al. | |
| 7,905,658 B2* | 3/2011 | Groβ ................ | A61B 6/4441 378/193 |
| 8,244,064 B2 | 8/2012 | Boese et al. | |
| 8,253,779 B2 | 8/2012 | Stetten | |

(Continued)

FOREIGN PATENT DOCUMENTS

CN   203220379 U   10/2013
CN   103417229 A   12/2013
(Continued)

OTHER PUBLICATIONS

U.S. Appl. No. 16/529,663, filed Aug. 1, 2019, Ferreira.

*Primary Examiner* — Kiho Kim
(74) *Attorney, Agent, or Firm* — Fletcher Yoder, P.C.

(57) ABSTRACT

A system is provided. The system includes a C-arm with an X-ray source and an X-ray detector mounted thereon opposite each other. The system also includes a carrier coupled to the C-arm and configured to rotate the C-arm relative to the carrier. The system further includes a base and a multiple robotic arms coupling the carrier to the base. Each robotic arm of the multiple robotic arms includes two articulated segments and at least two rotary joints.

20 Claims, 20 Drawing Sheets

(56) References Cited

U.S. PATENT DOCUMENTS

| | | | |
|---|---|---|---|
| 8,553,839 B2 | 10/2013 | Hendriks et al. | |
| 8,975,602 B2 | 3/2015 | Huber et al. | |
| 9,031,296 B2 | 5/2015 | Rapoport et al. | |
| 9,033,575 B2 | 5/2015 | Martinez Ferreira | |
| 9,147,551 B2 | 9/2015 | Luecken et al. | |
| 9,239,300 B2 | 1/2016 | Keeve et al. | |
| 9,271,684 B2 | 3/2016 | Knox et al. | |
| 9,398,675 B2* | 7/2016 | Eaves | A61B 6/4405 |
| 9,588,195 B2 | 3/2017 | Fichtinger et al. | |
| 9,610,056 B2 | 4/2017 | Lavallee et al. | |
| 9,687,308 B2 | 6/2017 | Windolf et al. | |
| 9,693,437 B2* | 6/2017 | Simmons | A61B 6/4405 |
| 9,943,962 B2 | 4/2018 | Saltier et al. | |
| 9,974,502 B2* | 5/2018 | Bouvier | A61B 6/548 |
| 10,028,788 B2* | 7/2018 | Kang | A61B 6/4441 |
| 10,034,716 B2 | 7/2018 | Crawford et al. | |
| 10,154,822 B2 | 12/2018 | Henderson et al. | |
| 10,338,238 B2 | 7/2019 | Kim et al. | |
| 10,426,414 B2 | 10/2019 | Weber et al. | |
| 2003/0164459 A1 | 9/2003 | Schardt et al. | |
| 2004/0003567 A1 | 1/2004 | Papalazarou et al. | |
| 2005/0228255 A1 | 10/2005 | Saracen et al. | |
| 2007/0211863 A1* | 9/2007 | Graumann | A61B 6/4441 378/197 |
| 2008/0004523 A1 | 1/2008 | Jensen | |
| 2008/0069309 A1 | 3/2008 | Doerre | |
| 2008/0123819 A1* | 5/2008 | Jensen | A61B 6/4405 378/198 |
| 2008/0130827 A1 | 6/2008 | Klingenbeck-Regn | |
| 2008/0159482 A1 | 7/2008 | Quaet-Faslem et al. | |
| 2008/0221478 A1 | 9/2008 | Ritchie et al. | |
| 2009/0296893 A1 | 12/2009 | Strobel | |
| 2010/0054414 A1 | 3/2010 | Herrmann | |
| 2010/0098214 A1 | 4/2010 | Star-Lack et al. | |
| 2011/0075809 A1* | 3/2011 | Boese | A61B 6/4014 378/92 |
| 2011/0280379 A1 | 11/2011 | Maschke | |
| 2011/0280380 A1 | 11/2011 | Maschke | |
| 2012/0085912 A1 | 4/2012 | McCroskey et al. | |
| 2012/0275571 A1 | 11/2012 | Neuber | |
| 2013/0077765 A1 | 3/2013 | Welsh | |
| 2013/0345718 A1 | 12/2013 | Crawford et al. | |
| 2015/0049856 A1* | 2/2015 | Ritschl | A61B 6/035 378/14 |
| 2015/0117601 A1 | 4/2015 | Keeve et al. | |
| 2015/0117603 A1 | 4/2015 | Keeve et al. | |
| 2015/0146862 A1 | 5/2015 | Kim | |
| 2015/0146863 A1 | 5/2015 | Kim | |
| 2015/0245882 A1 | 9/2015 | Venkatraghavan et al. | |
| 2015/0297311 A1 | 10/2015 | Tesar | |
| 2016/0027182 A1 | 1/2016 | Oh | |
| 2016/0089093 A1 | 3/2016 | Ying et al. | |
| 2016/0235493 A1 | 8/2016 | Crawford et al. | |
| 2016/0287198 A1 | 10/2016 | Abramovich | |
| 2016/0302871 A1 | 10/2016 | Gregerson et al. | |
| 2017/0135654 A1 | 5/2017 | van Daal et al. | |
| 2017/0172536 A1 | 6/2017 | Song et al. | |
| 2017/0188985 A1 | 7/2017 | Brudnick | |
| 2017/0209071 A1 | 7/2017 | Zhao et al. | |
| 2017/0258426 A1* | 9/2017 | Risher-Kelly | A61B 6/12 |
| 2018/0214100 A1 | 8/2018 | Kumar | |
| 2018/0289346 A1 | 10/2018 | van Beek et al. | |
| 2018/0008216 A1 | 11/2018 | Kim et al. | |

FOREIGN PATENT DOCUMENTS

| | | |
|---|---|---|
| CN | 104759033 A2 | 7/2015 |
| CN | 107802279 U | 3/2018 |
| DE | 102007044365 A1 | 3/2009 |
| DE | 102008032296 A1 | 1/2010 |
| DE | 102011080588 A1 | 2/2013 |
| DE | 202014219581 A1 | 9/2015 |
| DE | 102014208449 A1 | 11/2015 |
| JP | 3142079 U | 6/2018 |

\* cited by examiner

MOBILE X-RAY IMAGING SYSTEM INCLUDING A PARALLEL ROBOTIC STRUCTURE

BACKGROUND

The subject matter disclosed herein relates to X-ray imaging systems and, more particularly, to mobile X-ray imaging system gantries.

Medical diagnostic imaging systems generate images of an object, such as a patient, for example, through exposure to an energy source, such as X-rays passing through a patient, for example. The generated images may be used for many purposes. Often, when a practitioner takes X-rays of a patient, it is desirable to take several X-rays of one or more portions of the patient's body from a number of different positions and angles, and preferably without needing to frequently reposition the patient. To meet this need, C-arm X-ray diagnostic equipment has been developed. The term C-arm generally refers to an X-ray imaging device having a rigid and/or articulating structural member having an X-ray source and an image detector assembly that are each located at an opposing end of the structural member so that the X-ray source and the image detector face each other. The structural member is typically "C" shaped and so is referred to as a C-arm. In this manner, X-rays emitted from the X-ray source can impinge on the image detector and provide an X-ray image of the object or objects that are placed between the X-ray source and the image detector. However, the structure of the imaging system may limit movement of the C-arm.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In accordance with an embodiment, a system is provided. The system includes a C-arm with an X-ray source and an X-ray detector mounted thereon opposite each other. The system also includes a carrier coupled to the C-arm and configured to rotate the C-arm relative to the carrier. The system further includes a base and multiple robotic arms coupling the carrier to the base. Each robotic arm of the multiple robotic arms includes two articulated segments and at least two rotary joints.

In accordance with another embodiment, a mobile X-ray imaging system is provided. The mobile X-ray imaging system includes a C-arm with an X-ray source and an X-ray detector mounted thereon opposite each other. The system also includes a carrier coupled to the C-arm and configured to rotate the C-arm relative to the carrier. The system further includes a base and a parallel robotic structure including three robotic arms coupling the carrier to the base. Each robotic arm of the three robotic arms includes two articulated segments, two rotary joints, and a prismatic joint.

In accordance with a further embodiment, a mobile X-ray imaging system is provided. The mobile X-ray imaging system includes a C-arm with an X-ray source and an X-ray detector mounted thereon opposite each other. The system also includes a carrier coupled to the C-arm and configured to rotate the C-arm relative to the carrier. The system further includes a base and a parallel robotic structure including three robotic arms coupling the carrier to the base. Each robotic arm of the three robotic arms includes two articulated segments and three rotary joints.

BRIEF DESCRIPTION OF THE DRAWINGS

These and other features, aspects, and advantages of the disclosed subject matter will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The following embodiments describe an X-ray imaging system (e.g., mobile X-ray imaging system) including a C-arm that is coupled to the X-ray imaging system via a parallel robotic structure that provides extra functionality regarding the positioning of the C-arm. In addition to increasing a range of motion for the C-arm, the parallel robotic structure enables an increased range of motion for achieving a desired isocenter position. The parallel robotic structure may include a plurality of robotic arms (e.g., three robotic arms) that include a plurality of articulated segments and a plurality of joints (e.g., rotary joints). In certain embodiments, each robotic arm may include three rotary joints. In other embodiments, each robotic arm may include two rotary joints and a prismatic joint. Certain embodiments of the parallel robotic structure enable translation of an isocenter of the C-arm in both a vertical direction and a horizontal direction (e.g., relative to a surface that the imaging system is located on). In certain embodiments, the parallel robotic structure, in conjunction with rotation of the C-arm relative to a carrier coupling the C-arm to the parallel robotic structure, enables rotation of an X-ray source and an X-ray detector in a plane of the C-arm that is greater than 180 degrees (e.g. in an orbital direction).

Figure 1:
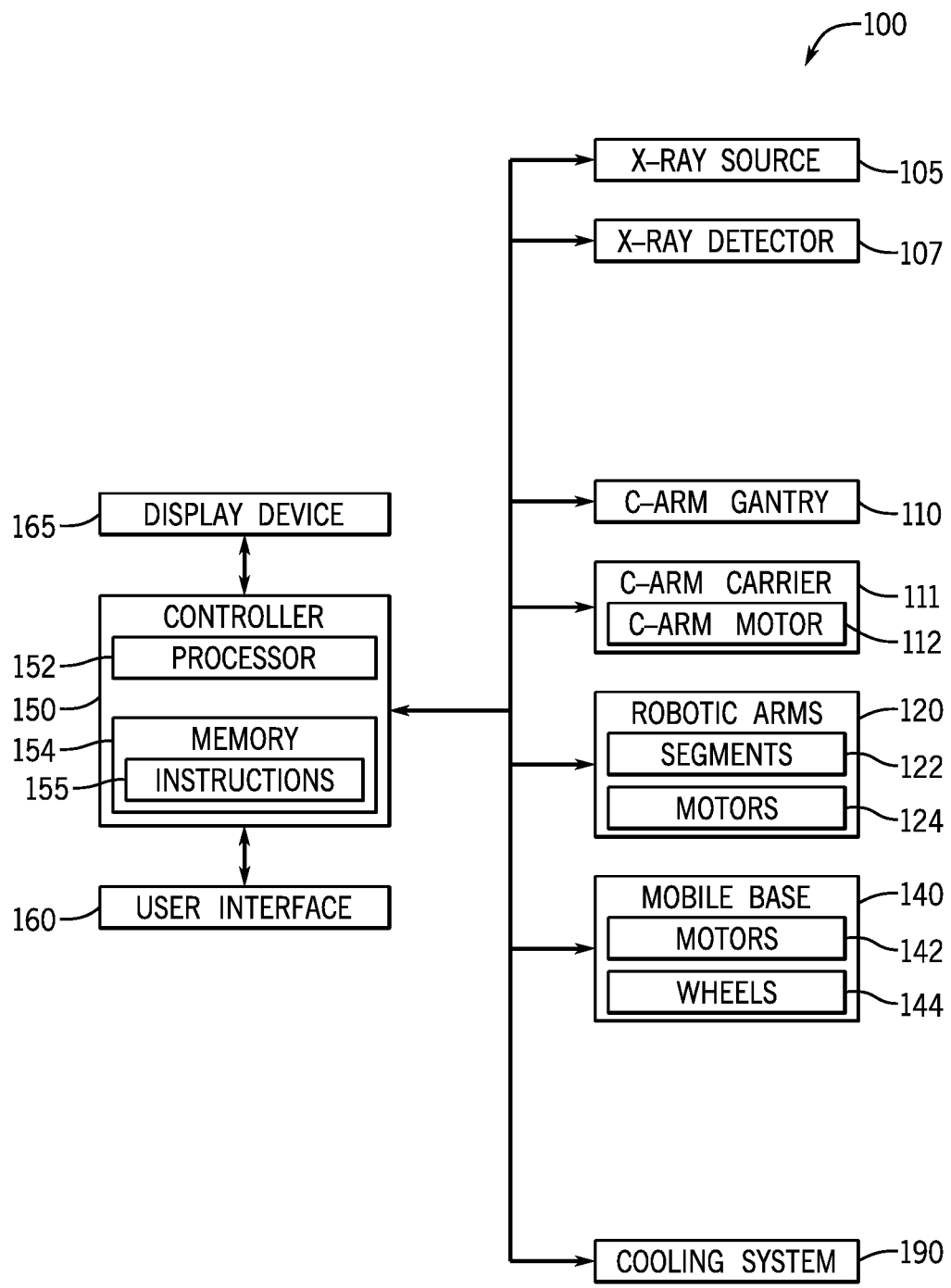
FIG. 1 is a block diagram illustrating components of an example mobile X-ray imaging system according to an embodiment.

FIG. 1 is a block diagram illustrating components of an example mobile X-ray imaging system 100. The mobile X-ray imaging system 100 includes an X-ray source 105 and an X-ray detector 107 mounted on a C-arm gantry 110.

The C-arm gantry 110 includes a C-arm motor 112 for adjusting the position of the C-arm gantry 110. More specifically, the C-arm gantry 110 is mechanically coupled to a C-arm carrier 111 which includes the C-arm motor 112, and the C-arm motor 112 may be driven to adjust the position of the C-arm gantry 110 with respect to the C-arm carrier 111, as described further below.

The mobile X-ray imaging system 100 further includes a plurality of robotic arms 120 mechanically coupled to the C-arm gantry 110 via the C-arm carrier 111. The robotic arms form a parallel robotic structure. Each robotic arm 120 includes a plurality of articulated segments or links 122 joined together via joints (e.g., rotary and/or prismatic joints). In certain embodiments, some of these joints may be associated with motors 124 (e.g., disposed within mobile base 140) as described further herein. In particular, each robotic arm 120 may include two articulated segments and three different joints. In a first configuration, each robotic arm 120 may include two rotary joints and a prismatic joint. In a second configuration, each robotic arm 120 may include three rotary joints.

The mobile base 140 includes one or more motors 142 for driving one or more wheels 144 to adjust a position of the mobile base 140. In addition, one or more of the wheels 144 may be free or un-motorized, as described further herein. For example, the wheels 144 may include two motorized wheels (with two motors 142 per motorized wheel) and one non-motorized wheel.

The mobile X-ray imaging system 100 further includes a controller 150 including a processor 152 and a non-transitory memory 154. A method for controlling the mobile X-ray imaging system 100 may be stored as executable instructions 155 in the non-transitory memory 154 and executed by the processor 152.

The mobile X-ray imaging system 100 further include a user interface 160 for receiving input from a user or operator of the mobile X-ray imaging system 100. The user interface 160 may be communicatively coupled to the controller 150 for providing commands input by a user via the user interface 160 to the controller 150. The user interface 160 may include one or more of a keyboard, a mouse, a trackball, one or more knobs, one or more joysticks, a touchpad, a touchscreen, one or more hard and/or soft buttons, a smartphone, a microphone, a virtual reality apparatus, and so on. The user interface 160 may thus enable voice control, and display of information such as simulated motion or possible collisions using the virtual reality apparatus or an interactive display device (e.g., touchscreen). In some examples the user interface 160 may be remotely located relative to the mobile X-ray imaging system 100. For example, the user interface 160 may be communicatively coupled to the controller 150 and/or the mobile X-ray imaging system 100 via a wired or wireless connection, and may be positioned away from the mobile base 140.

A user of the mobile X-ray imaging system 100 may input a desired isocenter position via the user interface 160, for example. The controller 150 may then determine position adjustments to one or more of the C-arm gantry 110, the robotic arms 120, and the mobile base 140 to align an isocenter of the mobile X-ray imaging system 100 with the desired isocenter position. As another example, a user of the mobile X-ray imaging system 100 may directly control the position of one or more components of the mobile X-ray imaging system 100 relative to other components of the mobile X-ray imaging system 100 via the user interface 160. For example, the user may directly input, via a joystick or knob, for example, position adjustments to one or more components of the mobile X-ray imaging system 100. As another example, the motion of the components of the mobile X-ray imaging system 100 may be pre-programmed such that the user does not directly control any movement, but instead initiates the start of the pre-programmed motion. The motion may comprise complex motions, with continuous motion of the isocenter.

The controller 150 is further communicatively coupled to a display device 165 for displaying one or more X-ray images acquired via the X-ray detector 107. Further, in some examples, one or more of the controller 150, the user interface 160, and the display device 165 may be positioned away from (e.g., remotely from) the remaining components of the mobile X-ray imaging system 100.

The mobile X-ray imaging system 100 may further include a cooling system 190 for cooling the X-ray source 105 and/or the X-ray detector 107. The cooling system 190 may include one or more flexible tubes and a pump, as an illustrative and non-limiting example, for providing cooling fluid to the X-ray source 105 to transfer thermal energy away from the X-ray source 105. The cooling system 190 may actively cool the X-ray source 105 and the X-ray detector 107 independently, or in some examples may cool the X-ray detector 107 by any suitable type of derivation of the cooling circuit for the X-ray source 105.

Figure 2:
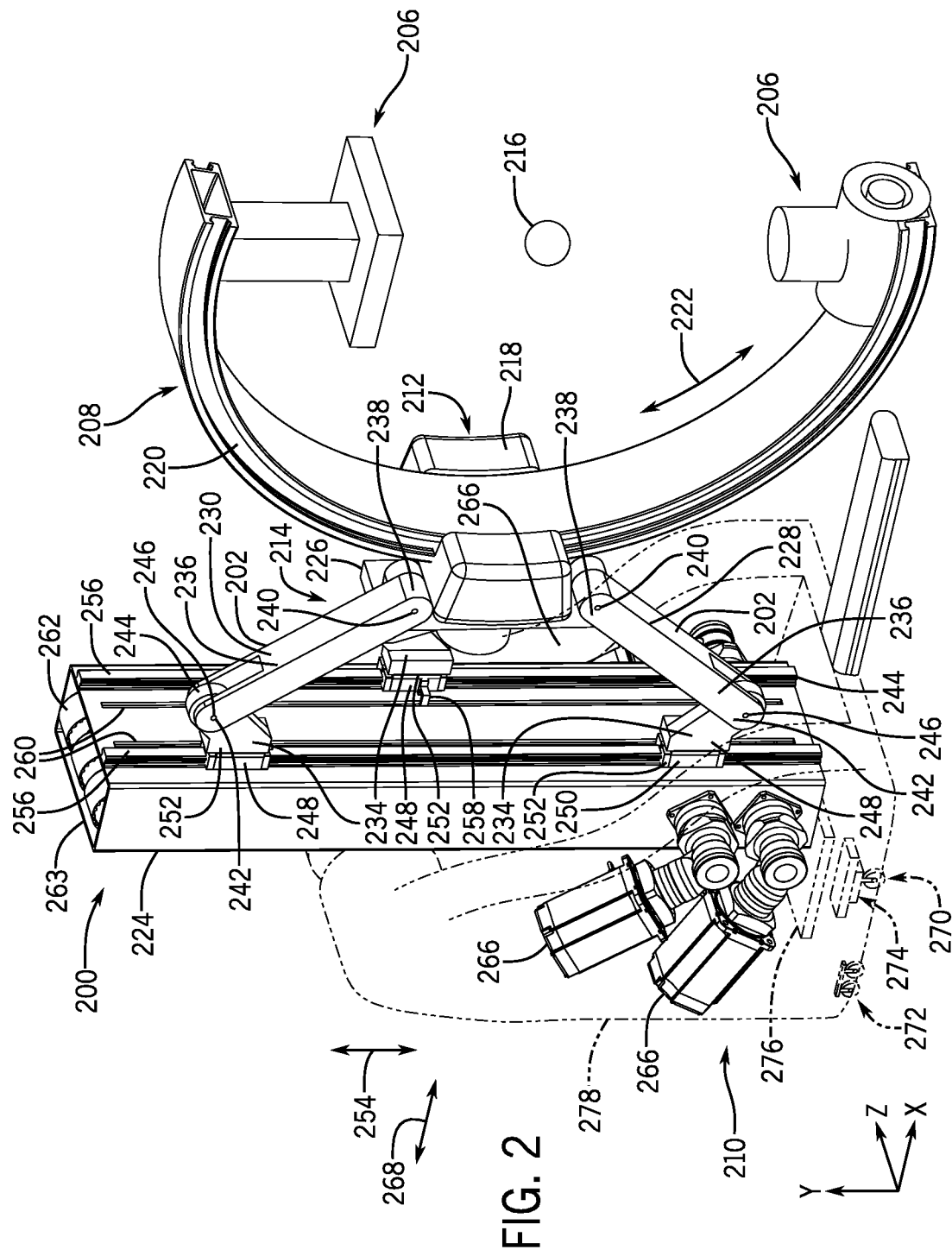
FIG. 2 is a perspective view of an embodiment of a mobile X-ray imaging system (e.g., with each robotic arm including two rotary joints and a prismatic joint)
Figure 3:
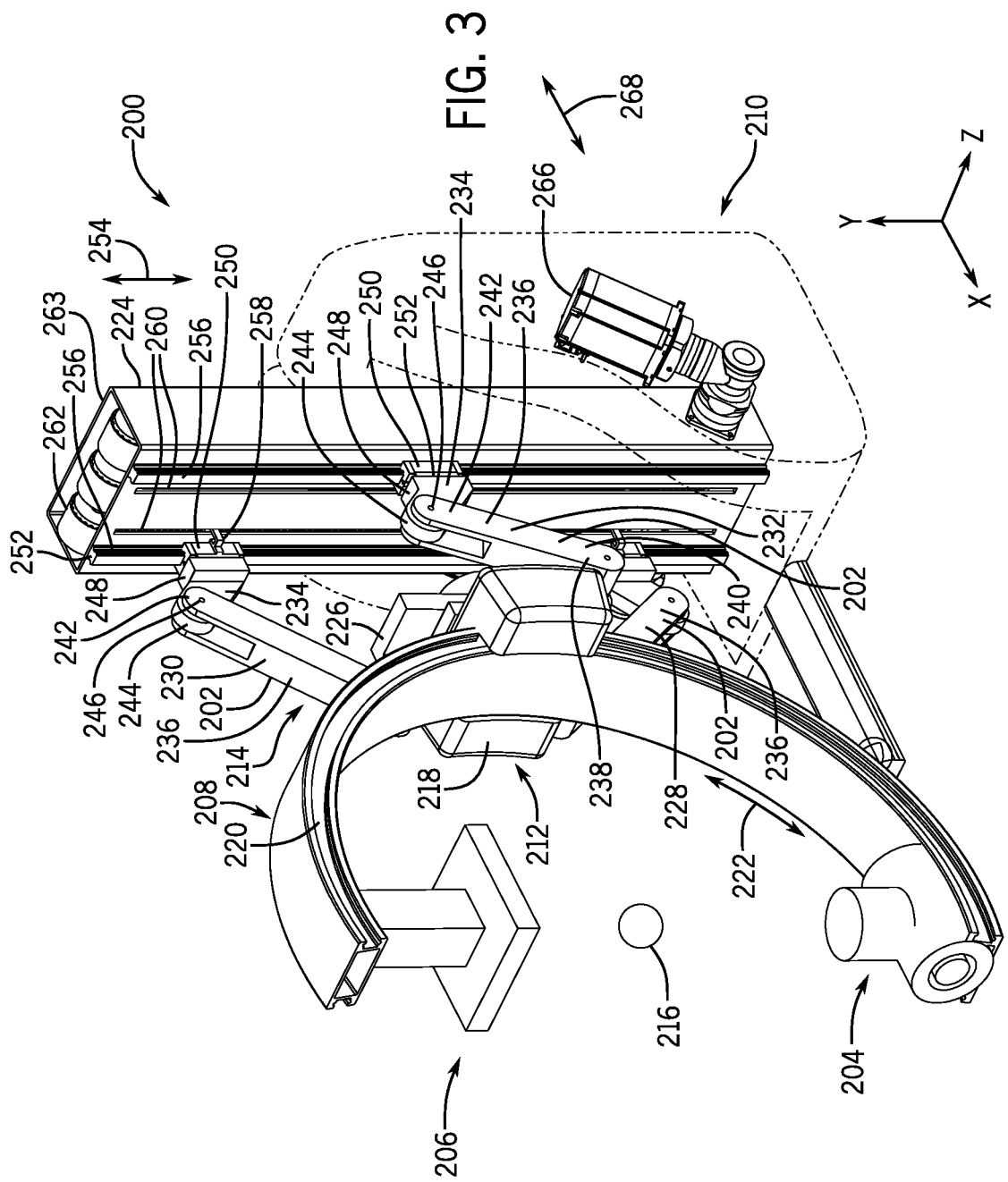
FIG. 3 is another perspective view of an embodiment of the mobile X-ray imaging system of FIG. 2.

FIGS. 2 and 3 are perspective views of an embodiment of a mobile X-ray imaging system 200 (e.g., with each robotic arm 202 including two rotary joints and a prismatic joint). The mobile X-ray imaging system 200 includes the components depicted in FIG. 1. For example, the mobile X-ray imaging system 200 includes the X-ray source 204 and the X-ray detector 206 mounted on a C-arm gantry 208. The C-arm gantry 208 is coupled to a mobile base 210 of the mobile X-ray imaging system 200 via a C-arm carrier 212 and a parallel robotic structure 214. As described herein, the C-arm carrier 212 and the parallel robotic structure 214 may be controlled to adjust a position of an imaging isocenter 216, also referred to herein simply as isocenter 216, relative to mobile base 210, to adjust a position of the C-arm gantry 208 relative to the mobile base 210, and/or to adjust a position of the X-ray source 204 and the X-ray detector 206 relative to the isocenter 216. To be specific, the isocenter 216 of the C-arm gantry 208 includes the intersection of the optical axis (defined by a focus of the X-ray source 204 and the center of the X-ray detector 206 or the normal to the X-ray detector 206 that goes through the focus) and the C-arm rotation axis along the carrier 212.

The C-arm carrier 212 includes a carrier base 218 coupled to the C-arm gantry 208 and configured to rotate the C-arm gantry 208 along a gantry track 220 in the depicted x-y plane. To that end, the carrier base 218 may include one or more motors (not shown), such as the C-arm motor, for sliding the C-arm gantry 208 along the gantry track 220. The C-arm gantry 208 may be rotated in the x-y plane about a rotation axis or the isocenter 216 relative to the C-arm carrier 212 (e.g., in an orbital direction 222), such that the X-ray source 204 and the X-ray detector 206 are rotated relative to the isocenter 216 in the x-y plane.

As mentioned above, the C-arm gantry 208 is coupled to the mobile base 210 via the C-arm carrier 212 and the parallel robotic structure 214. The parallel robotic structure 214 includes a plurality of robotic arms 202 coupled to and extending between a vertical tower 224 of the mobile base 210 and a support base 226 coupled to the carrier base 218. As depicted, the parallel robotic structure 214 includes three robotic arms 202 (e.g., robotic arms 228, 230, 232). In certain embodiments, the number of robotic arms 202 may vary (e.g., 2, 3, 4, etc.). Each robotic arm 202 includes two articulated segments 234, 236. In certain embodiments, the number of articulated segments in each robotic arm 202 may vary (e.g., 2, 3, 4, etc.). As depicted, an end 238 of the articulated segment 236 for each robotic arm 202 is coupled to the support base 226 via a joint 240 (e.g., rotary joint). The joint 240 is non-motorized and enables rotation of the articulated segment 236 about the joint 240 relative to the support base 226 in the depicted x-y plane. An end 242 of the articulated segment 236 for each robotic arm 202 is coupled to an end 244 of the articulated segment 234 via a joint 246 (e.g., rotary joint). In particular, the end 242 flanks the end 244. The joint 246 is non-motorized and enables rotation of the articulated segment 236 about the joint 246 relative to the articulated segment 234 in the depicted x-y plane. Both rotary joints 240, 246 are passive joints.

Figure 4:
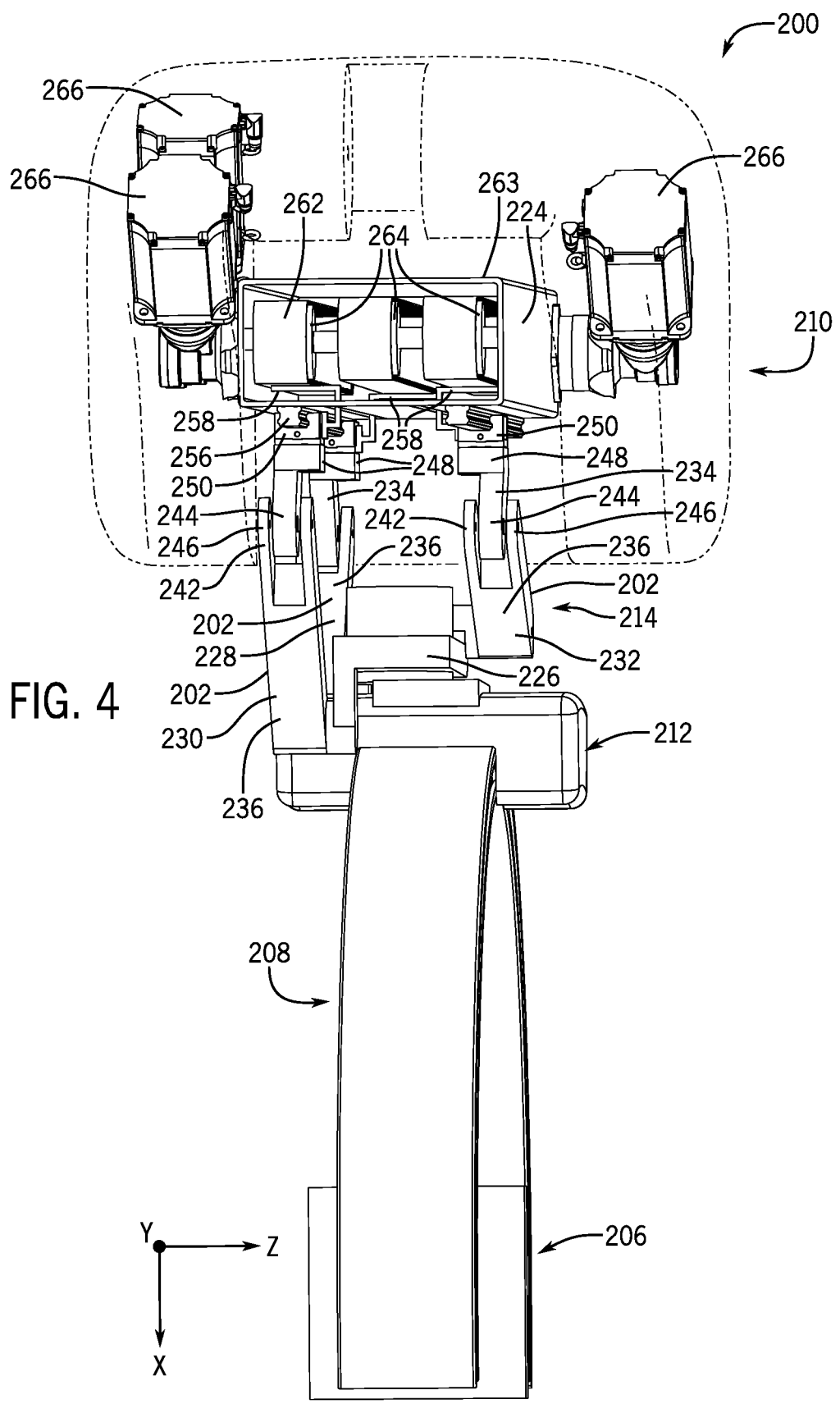
FIG. 4 is a top perspective view of an embodiment of a portion of the mobile X-ray system of FIG. 2.

An end 248 of the articulated segment 234 (opposite of the end 244) of each robotic arm 202 is coupled to a respective sliding base 250 coupled to the vertical tower 224. The end 248 of the articulated segment 234 and the sliding base 250 form a joint 252 (e.g., prismatic joint). The vertical tower 224 enables movement or translation (indicated by arrow 254) of the articulated segment 234 of each robotic arm 202. Each sliding base 250 is disposed about a respective vertical guide 256 that guides movement of the sliding base 250. As depicted, the robotic arms 228, 230 share the same respective vertical guide 256. In certain embodiments, each robotic arm 202 may move along its own vertical guide 256. As depicted in FIG. 4, each sliding base 250 includes an extension 258 that extends through a slot 260 into the vertical tower 224 and engages a respective conveyor belt 262 disposed within a wall 263 of the vertical tower 224. The extensions 258 for the sliding bases 250 associated with robotic arms 228, 230 extend through the same slot 260, while the extension 258 for the sliding base 250 associated with robotic arm 232 extends through a different slot 250. In certain embodiments, the extensions 258 for the sliding bases 250 associated with the robotic arms 202 may extend through different slots 260. Each conveyor belt 262 is disposed about rollers 264. As depicted, three conveyor belts 262 are disposed within the vertical tower 224. In certain embodiments, the conveyor belts 262 make include protrusions to engage the extensions 258. Motors 266 are disposed with the mobile base 210 to control the movement of the belts 262 and, thus, the robotic arms 202 of the parallel robotic structure 214 via translations of the sliding bases 250 and the robotic arms 202.

Figure 5:
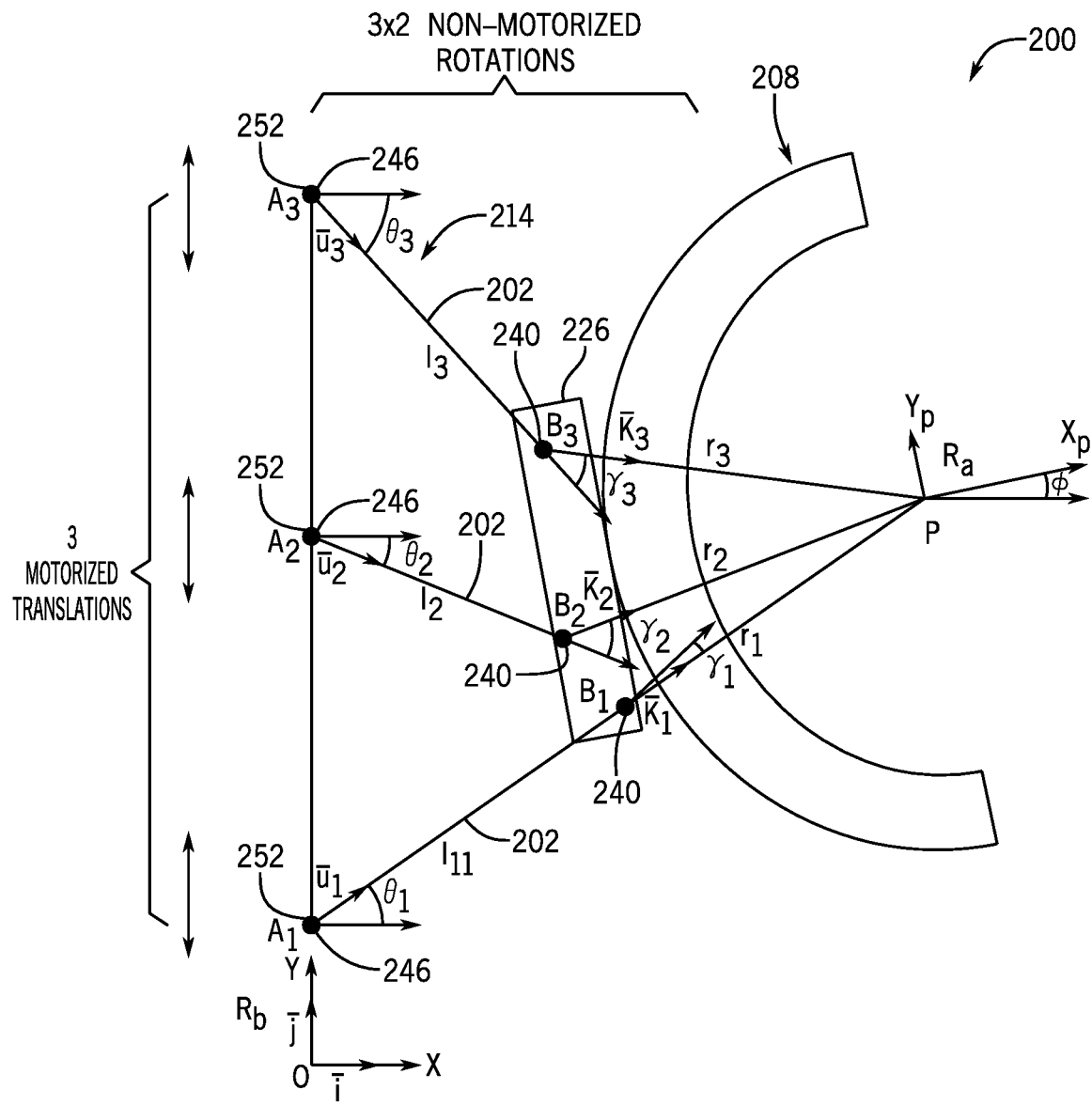
FIG. 5 is a schematic diagram illustrating translations and rotations of the robotic arms of the mobile X-ray imaging system of FIG. 2.

Translation of the sliding bases 250 and the robotic arms 202, in conjunction with rotation about the joints 240, 246 rotates the carrier base 218 and the C-arm gantry 208 coupled to the carrier base 218 about the isocenter 216 in three-dimensional space (e.g., in the x-y plane). As noted above, rotation of the C-arm gantry 208 may also occur in the x-y plane via the C-arm carrier 212. Translation of the sliding bases 250 and the robotic arms 202, in conjunction with rotation about the joints 240, 246 may also adjust a height (e.g., in the vertical direction 254) and a depth (e.g., in horizontal direction 268) of the C-arm gantry 208 and the isocenter 216. FIG. 5 depicts the movement of the robotic arms 202 of the imaging system 200 via the rotary joints 240, 246 (via non-motorized rotations) and prismatic joints 252 (motorized translations) that enable movement of the C-arm gantry 208 and the isocenter 216. The parallel robotic structure 214, along with rotation of the C-arm gantry 208 with the C-arm carrier 212, provide three degrees of freedom for movement (e.g., with regard to vertical, depth, and rotation) for the C-arm gantry 208. The ranges of the angles of rotation at the joints 240, 246 is theoretical. The rotation of C-arm gantry 208, in conjunction with the movement of the robotic arms 202, enables a rotation of the X-ray source 204 and the X-ray detector 206 of more than 180 degrees in the plane of C-arm gantry 208 (e.g., orbital direction 222).

Figure 6:
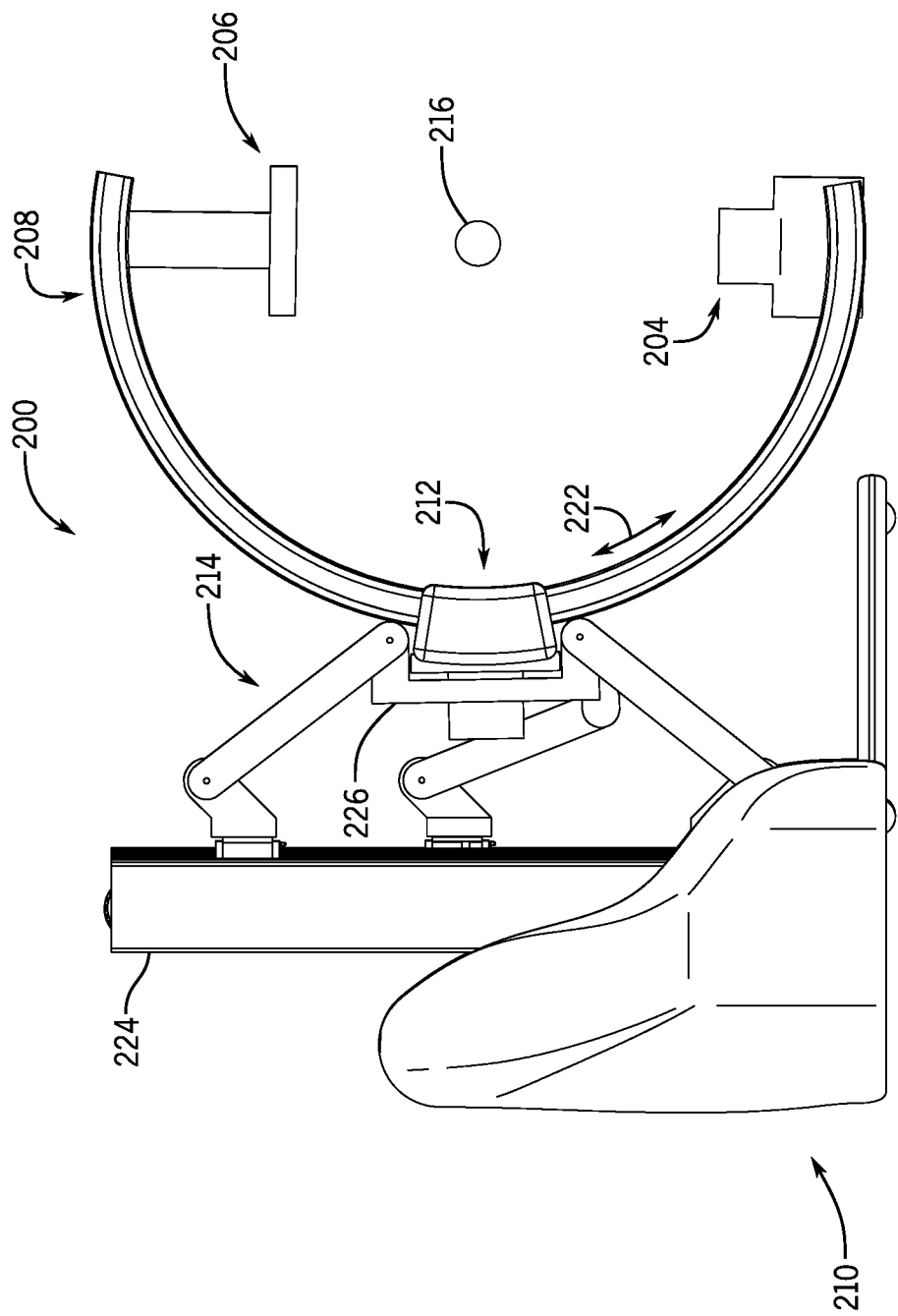
FIGS. 6-8 illustrate movement of a C-arm of the mobile X-ray imaging system of FIGS. 2 and 3 according to an embodiment.
Figure 7:
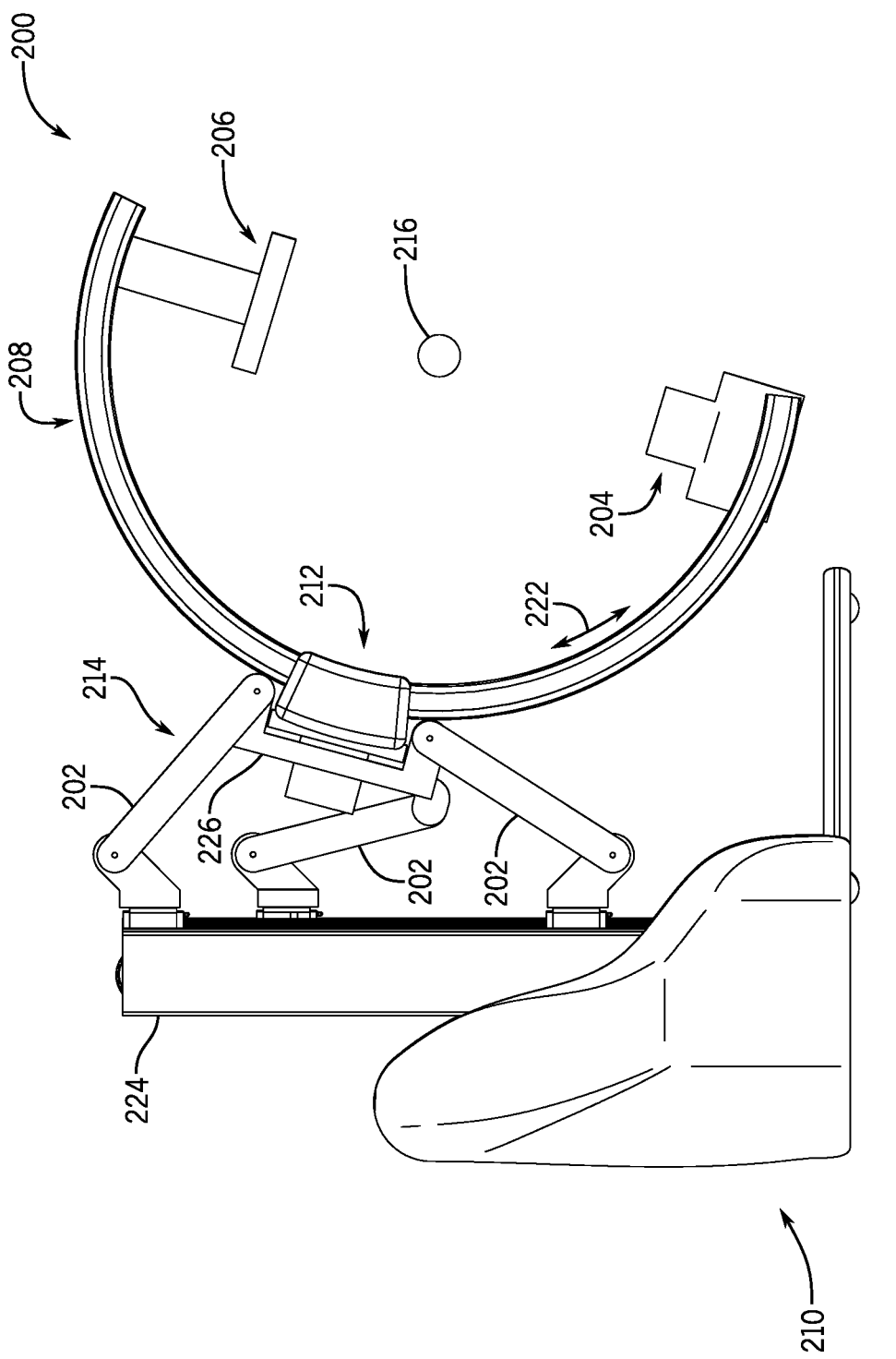
Figure 8:
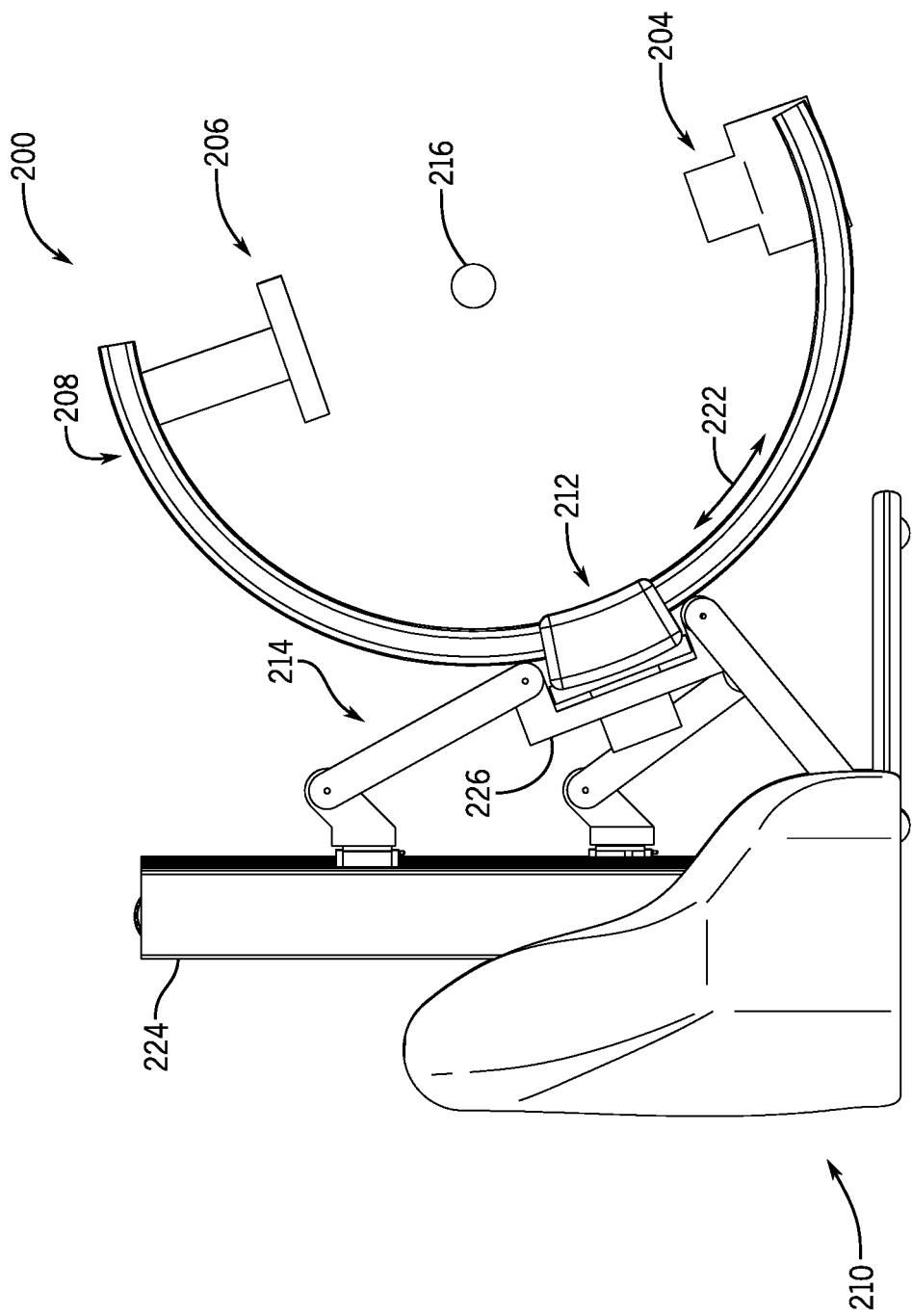

FIGS. 6-8 illustrate movement of the C-arm gantry 208 of the mobile X-ray imaging system 200 of FIGS. 2 and 3 utilizing the parallel robotic structure 214. For example, as depicted in FIGS. 6 and 7, the parallel robotic structure 214 is utilized to rotate the C-arm gantry 208 in the x-y plane (i.e., orbital direction 222) so that the X-ray detector 206 is rotated away from the mobile base 210. As depicted in transitioning from FIG. 7 to FIG. 6 and then to FIG. 8. The parallel robotic structure 214 is utilized to rotate the C-arm gantry 208 in the x-y plane (i.e., orbital direction 222) so that the X-ray detector 206 is rotated toward the mobile base 210.

Returning to FIG. 2 (for simplicity items not shown in FIG. 3), the mobile base 210 includes a plurality of wheels including driven wheels 270 and free wheels 272. The driven wheels 270 may be driven by one or more motors 274 for moving the mobile base 210 and thus the entire mobile X-ray imaging system 200. In addition to moving the mobile X-ray imaging system 200 along the x-axis (i.e., to the left and right), the motor 274 may drive the driven wheels 270 in the z direction, thus enabling the mobile X-ray imaging system 200 to be re-positioned in any orientation in the x-z plane. As an example, two motors 274 for each of the driven wheels 270 may be provided, wherein one motor 274 includes a traction motor and a second motor 274 includes a direction motor. In other examples, dual wheels (with differential traction motors), omnidirectional wheels, or other types of motorized wheels may be used. The free wheels 272 may not be driven by a motor. Further, as depicted, the driven wheels 270 may be positioned in the front of the mobile base 210 (i.e., on the side of the mobile base 210 closer to the C-arm gantry 208) and thus may be advantageously positioned closer to the center of gravity of the mobile X-ray imaging system 200. In some embodiments, the free wheels 272 may be positioned at the front side of the mobile base 210 on a structure extending towards the C-arm gantry 208. In some examples, all wheels of the mobile X-ray imaging system 200 may be driven wheels 270.

In some examples, the mobile X-ray imaging system 200 may include a high voltage generator 276 housed within a housing 278 of the mobile base 210. Providing the high voltage generator 276 within the mobile base 210 increases the weight of the mobile base 210, thus stabilizing the mobile X-ray imaging system 200. Furthermore, providing the high voltage generator 276 within the mobile base 210 avoids housing the high voltage generator 276 remotely from the mobile X-ray imaging system 200, thereby eliminating long high-voltage cables typically connected to the X-ray source 204 via a tether for providing the X-ray source 204 with high voltages.

Figure 9:
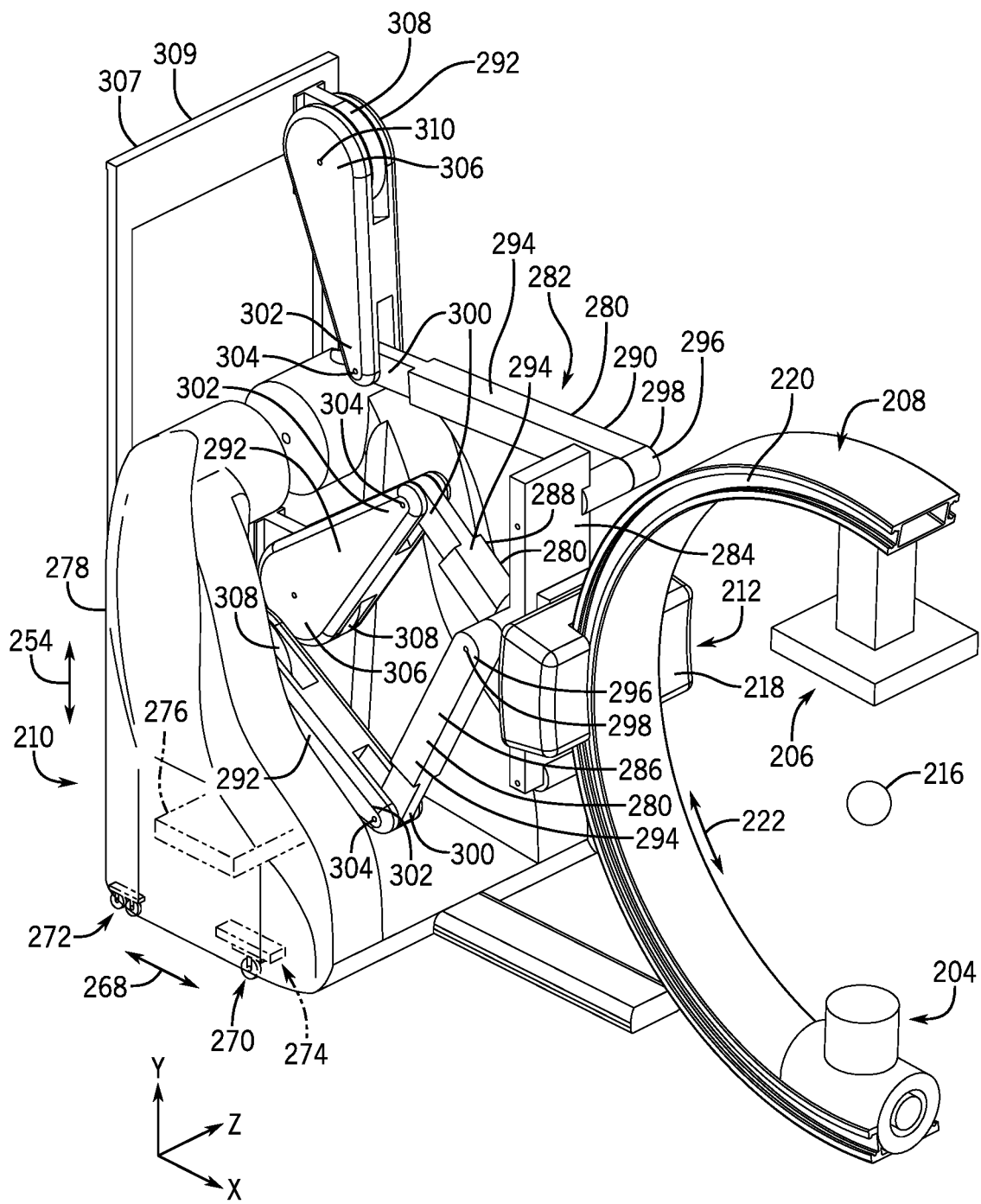
FIG. 9 is a perspective view of an embodiment of a mobile X-ray imaging system (e.g., with each robotic arm including three rotary joints)
Figure 10:
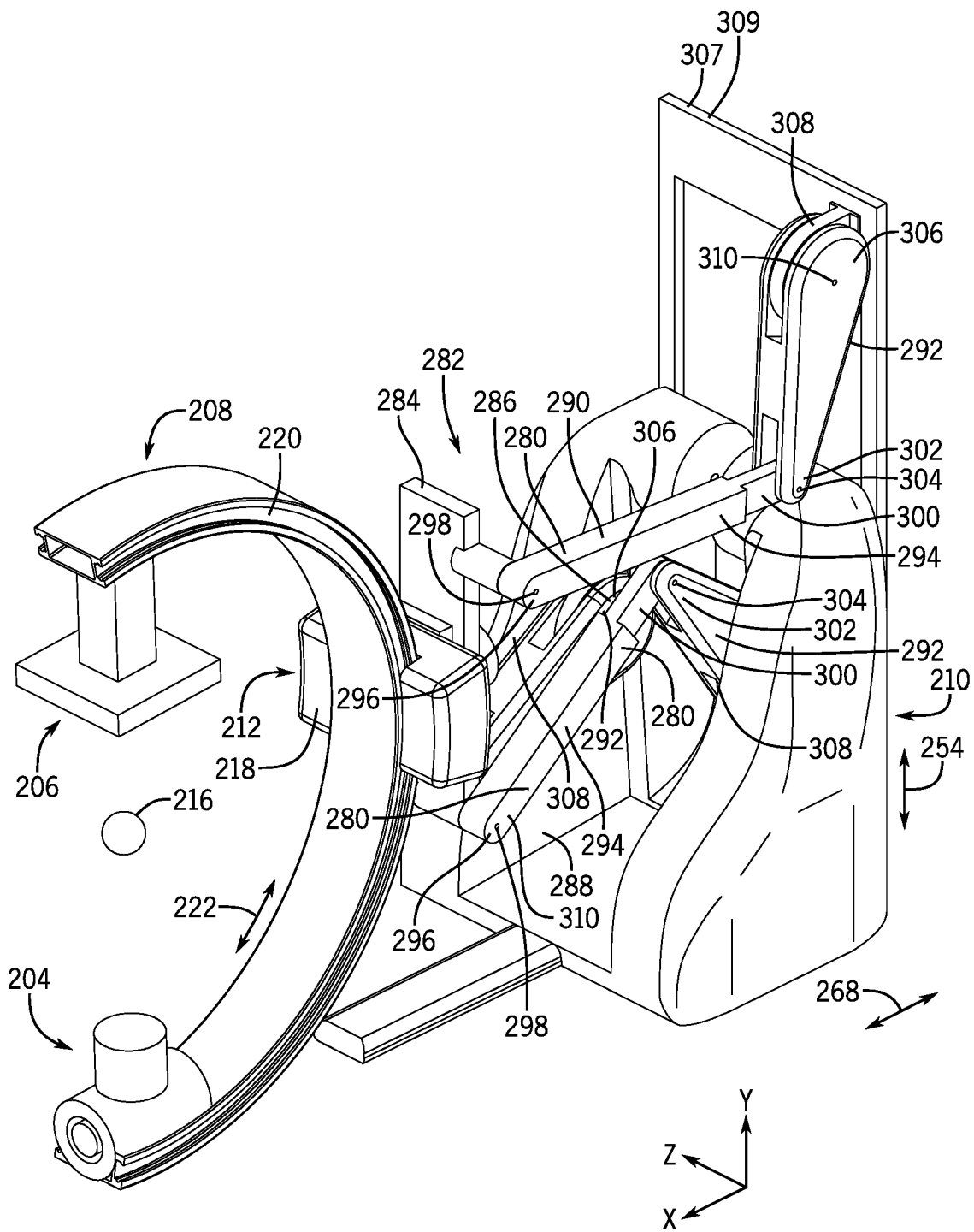
FIG. 10 is another perspective view of an embodiment of the mobile X-ray imaging system of FIG. 9.

FIGS. 9 and 10 are perspective views of an embodiment of a mobile X-ray imaging system 200 (e.g., with each robotic arm 280 including three rotary joints). The mobile X-ray imaging system 200 includes the components depicted in FIG. 1. For example, the mobile X-ray imaging system 200 includes the X-ray source 204 and the X-ray detector 206 mounted on a C-arm gantry 208. The C-arm gantry 208 is coupled to a mobile base 210 of the mobile X-ray imaging system 200 via a C-arm carrier 212 and a parallel robotic structure 282. As described herein, the C-arm carrier 212 and the parallel robotic structure 282 may be controlled to adjust a position of an imaging isocenter 216, also referred to herein simply as isocenter 216, relative to mobile base 210, to adjust a position of the C-arm gantry 208 relative to the mobile base 210, and/or to adjust a position of the X-ray source 204 and the X-ray detector 206 relative to the isocenter 216. To be specific, the isocenter 216 of the C-arm gantry 208 includes the intersection of the optical axis (defined by a focus of the X-ray source 204 and the center of the X-ray detector 206 or the normal to the X-ray detector 206 that goes through the focus) and the C-arm rotation axis along the carrier 212.

The C-arm carrier 212 includes a carrier base 218 coupled to the C-arm gantry 208 and configured to rotate the C-arm gantry 208 along a gantry track 220 in the depicted x-y plane. To that end, the carrier base 218 may include one or more motors (not shown), such as the C-arm motor, for sliding the C-arm gantry 208 along the gantry track 220. The C-arm gantry 208 may be rotated in the x-y plane about a rotation axis or the isocenter 216 relative to the C-arm carrier 212 (e.g., in an orbital direction 222), such that the X-ray source 204 and the X-ray detector 206 are rotated relative to the isocenter 216 in the x-y plane.

As mentioned above, the C-arm gantry 208 is coupled to the mobile base 210 via the C-arm carrier 212 and the parallel robotic structure 282. The parallel robotic structure 282 includes a plurality of robotic arms 280 coupled to and extending between the mobile base 210 and a support base 284 coupled to the carrier base 218. As depicted, the parallel robotic structure 282 includes three robotic arms 280 (e.g., robotic arms 286, 288, 290). In certain embodiments, the number of robotic arms 280 may vary (e.g., 2, 3, 4, etc.). Each robotic arm 280 includes two articulated segments 292, 294. In certain embodiments, the number of articulated segments in each robotic arm 280 may vary (e.g., 2, 3, 4, etc.). As depicted, an end 296 of the articulated segment 294 for each robotic arm 280 is coupled to the support base 284 via a joint 298 (e.g., rotary joint). The joint 298 is non-motorized and enables rotation of the articulated segment 294 about the joint 298 relative to the support base 284 in the depicted x-y plane. An end 300 of the articulated segment 294 for each robotic arm 280 is coupled to an end 302 of the articulated segment 292 via a joint 304 (e.g., rotary joint). In particular, the end 302 flanks the end 300. The joint 304 is non-motorized and enables rotation of the articulated segment 292 about the joint 304 relative to the articulated segment 294 in the depicted x-y plane. Both rotary joints 298, 304 are passive joints.

An end 306 of the articulated segment 292 (opposite of the end 302) of each robotic arm 280 is coupled to a respective support 308 coupled to a respective rotation actuator (not shown) coupled to respective motors (not shown) within the mobile base 210. The support 308 for the robotic arm 290 is coupled to a horizontal portion 307 of a vertical extension 309 of the mobile base 210. In particular, the end 306 flanks the support 308. The end 306 of the articulated segment 292 and the support 308 form a joint 310 (e.g., rotary joint). The rotation actuators enable rotation about the three rotary joints 298, 304, 310 of the robotic arms 280.

Figure 11:
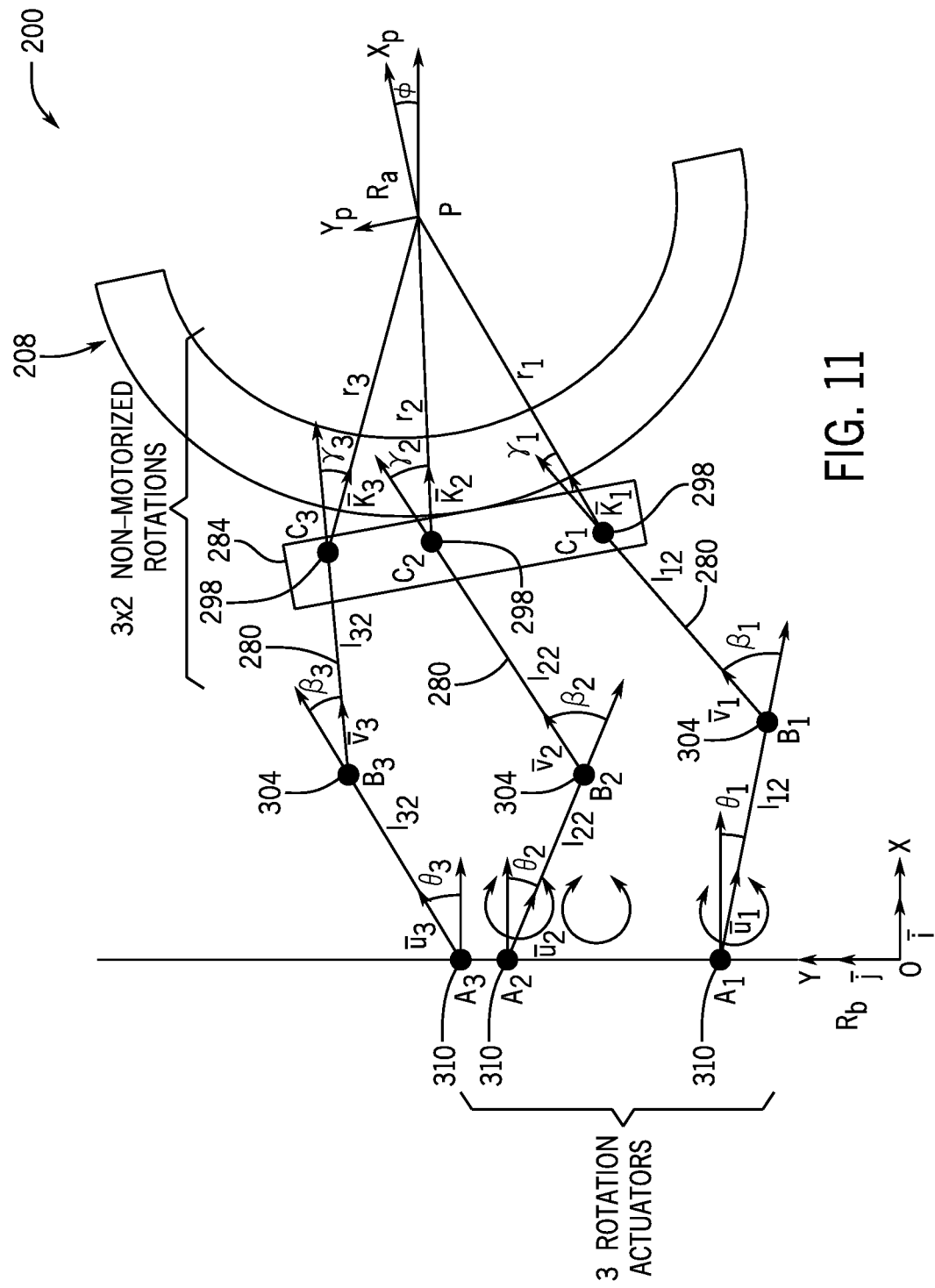
FIG. 11 is a schematic diagram illustrating rotations of the robotic arms of the mobile X-ray imaging system of FIG. 9.

Rotation about the joints 298, 304, 310 of the robotic arms 280 rotates the carrier base 218 and the C-arm gantry 208 coupled to the carrier base 218 about the isocenter 216 in three-dimensional space (e.g., in the x-y plane). As noted above, rotation of the C-arm gantry 208 may also occur in the x-y plane via the C-arm carrier 212. Rotation about the joints 298, 304, 310 of the robotic arms 280 may also adjust a height (e.g., in the vertical direction 254) and a depth (e.g., in horizontal direction 268) of the C-arm gantry 208 and the isocenter 216. FIG. 11 depicts the movement of the robotic arms 280 of the imaging system 200 via the rotary joints 298, 304, 310 (via non-motorized rotations) that enable movement of the C-arm gantry 208 and the isocenter 216. The parallel robotic structure 282, along with rotation of the C-arm gantry 208 with the C-arm carrier 212, provide three degrees of freedom for movement (e.g., with regard to vertical, depth, and rotation) for the C-arm gantry 208. The ranges of the angles of rotation at the joints 298, 304, 310 is theoretical. The rotation of C-arm gantry 208, in conjunction with the movement of the robotic arms 280, enables a rotation of the X-ray source 204 and the X-ray detector 206 of more than 180 degrees in the plane of C-arm gantry 208 (e.g., orbital direction 222).

Figure 12:
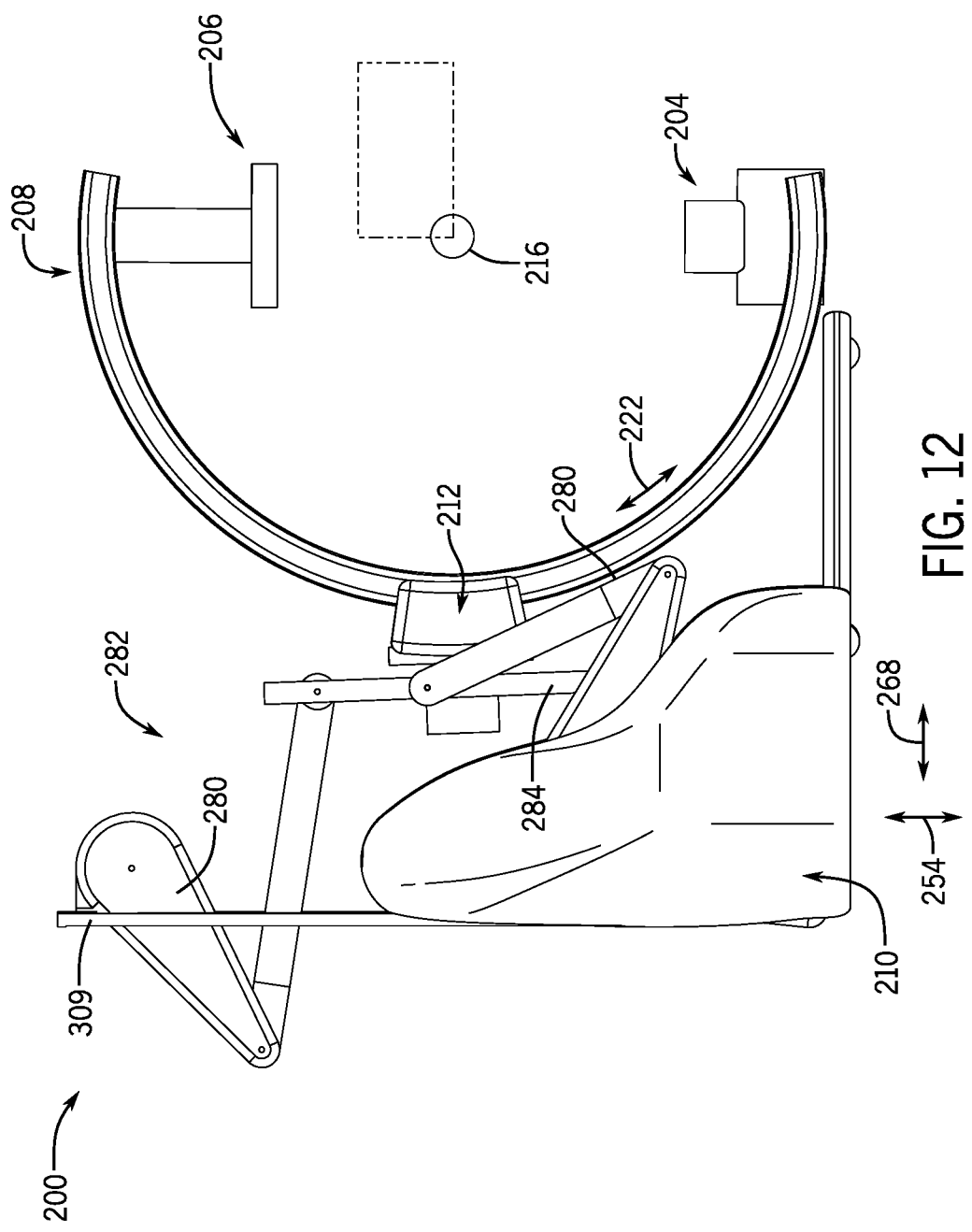
FIGS. 12-20 illustrate movement and translation of the C-arm of the mobile X-ray imaging system of FIG. 9 and translation of the isocenter according to an embodiment.
Figure 13:
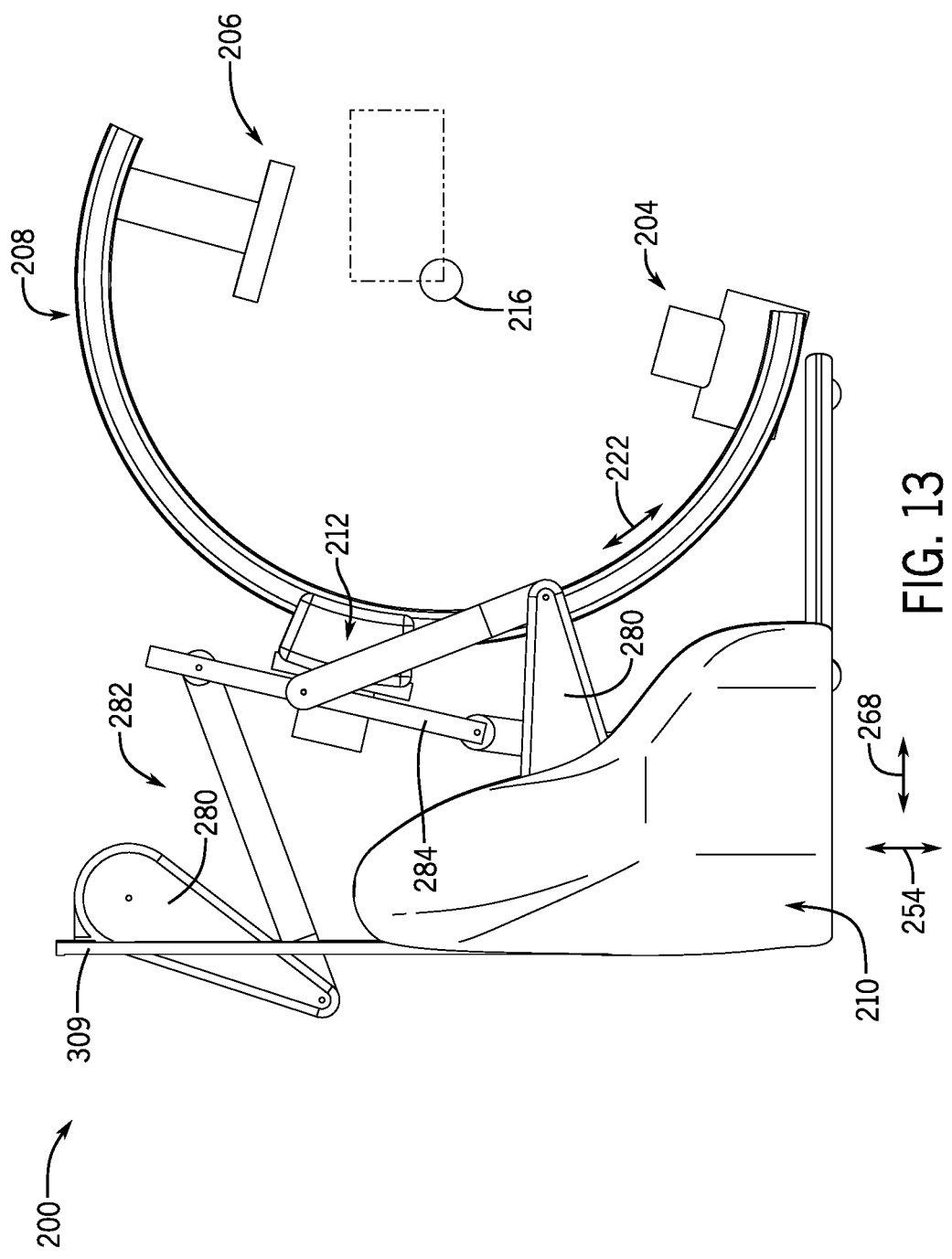
Figure 14:
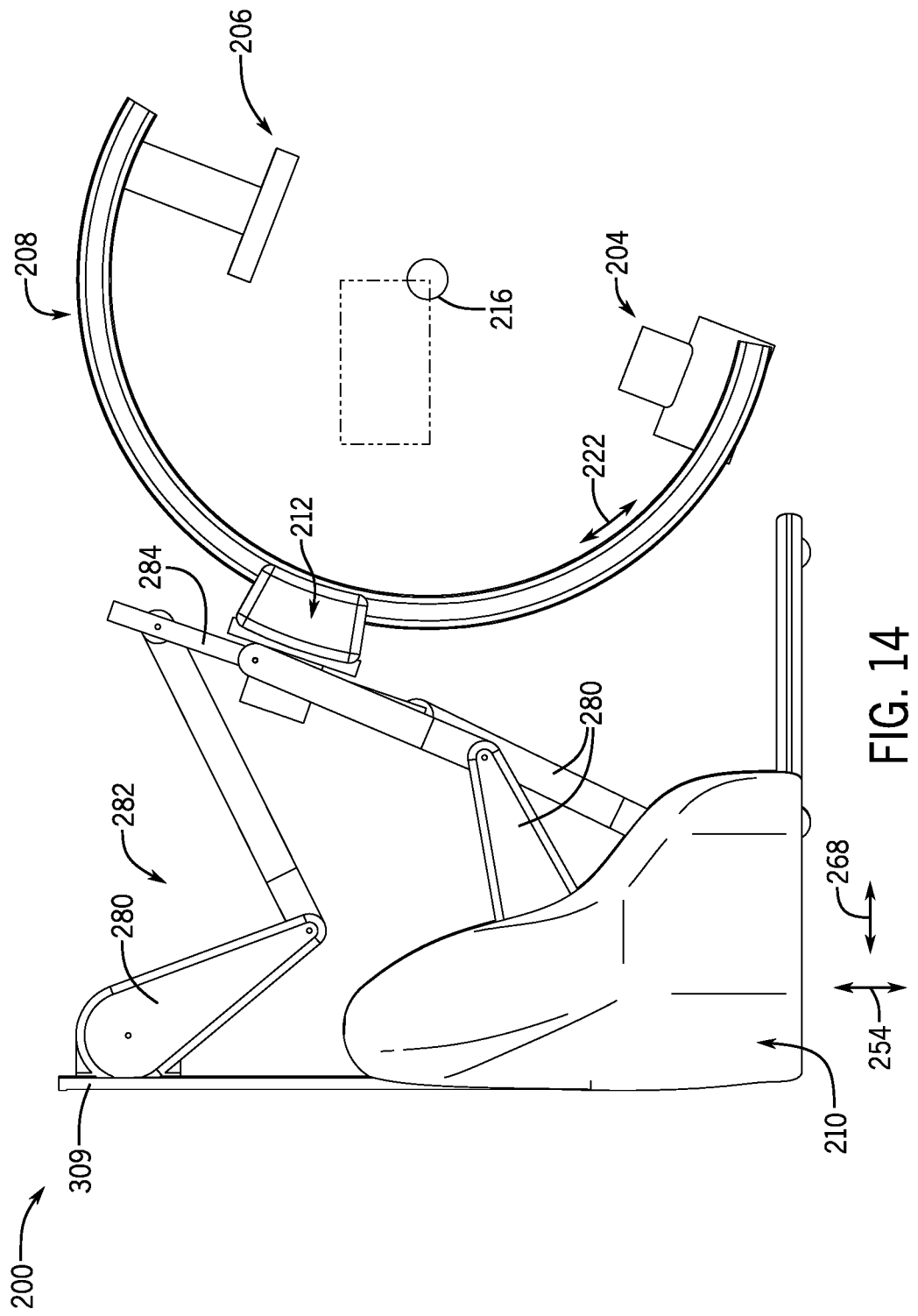
Figure 15:
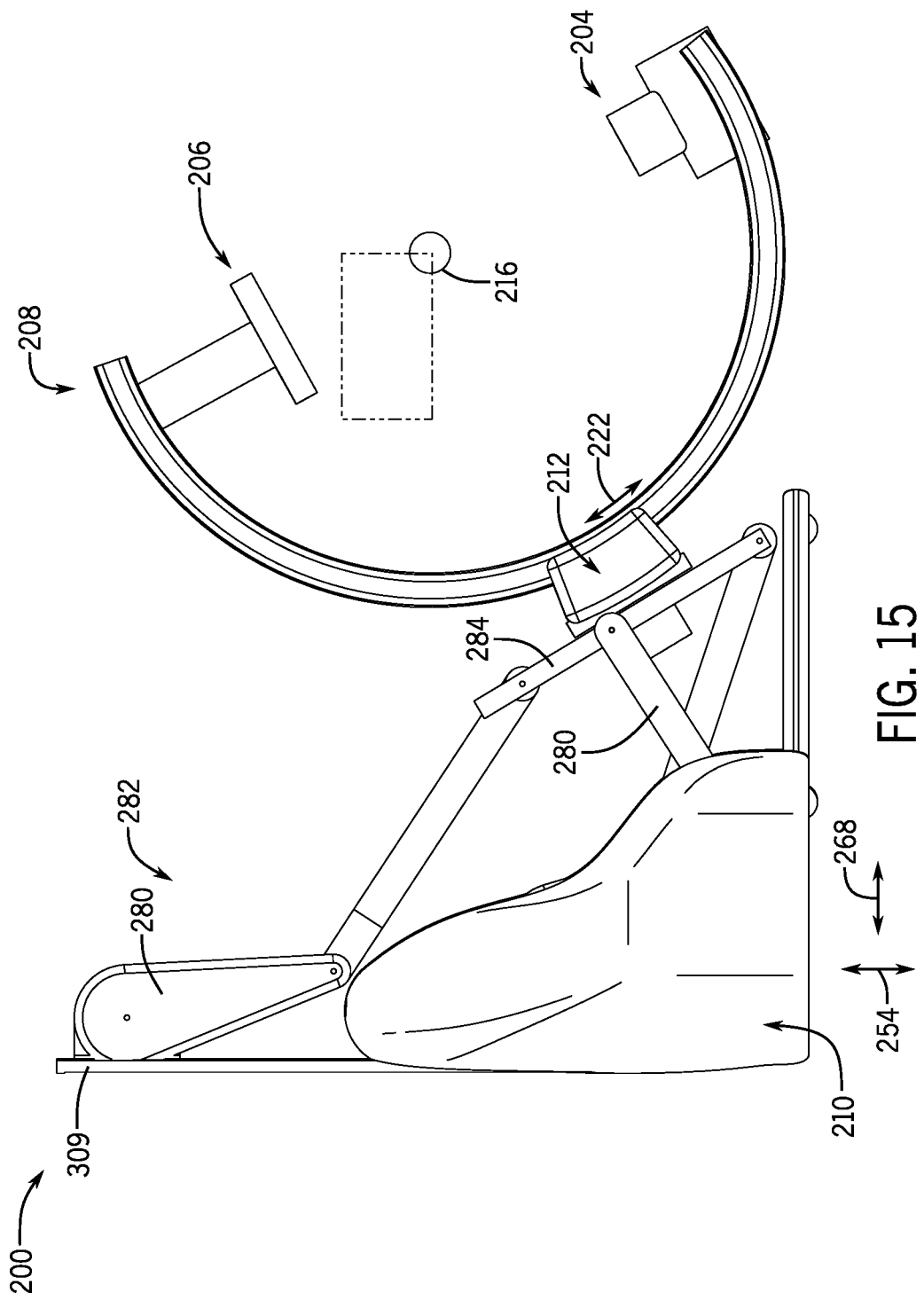
Figure 16:
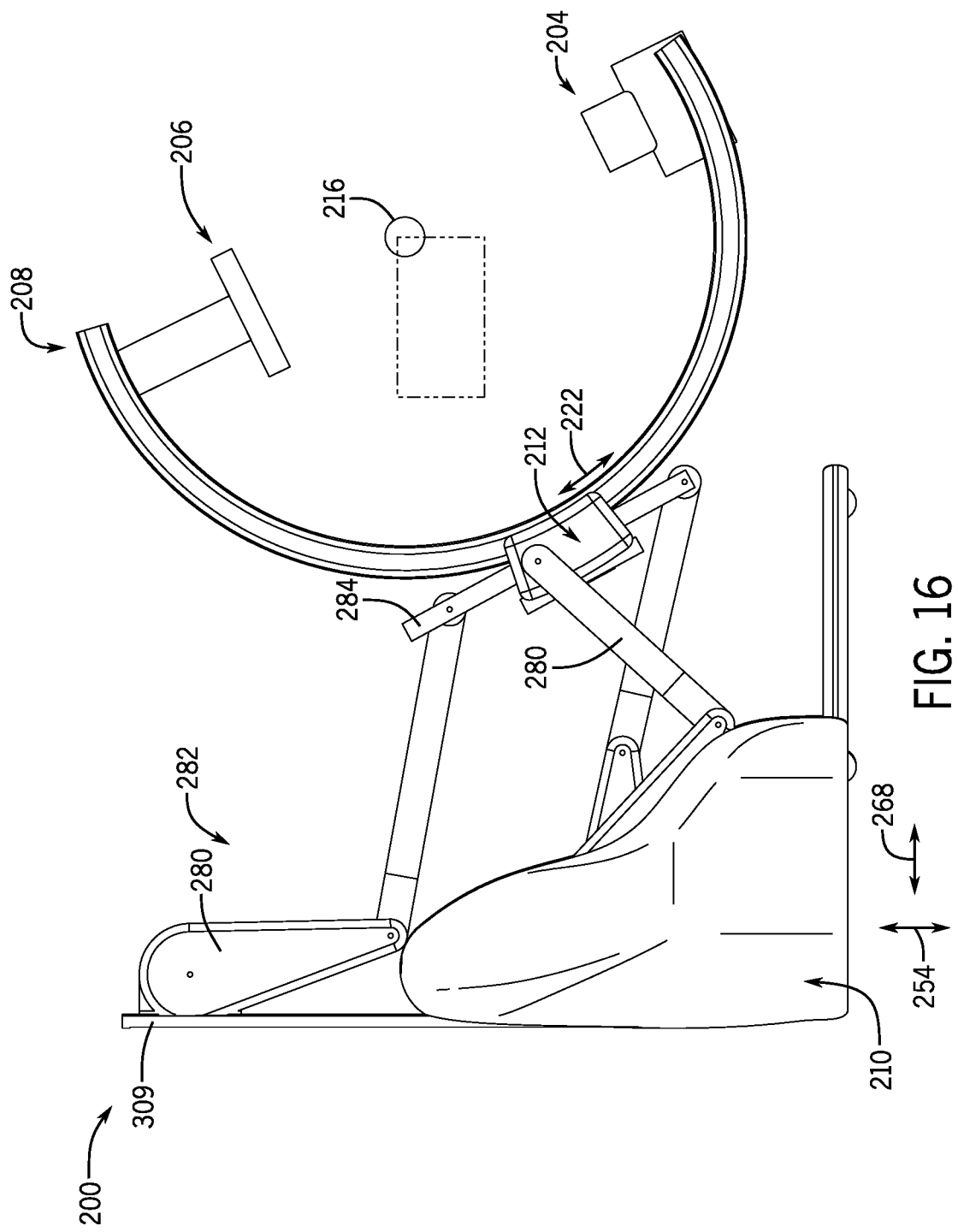
Figure 17:
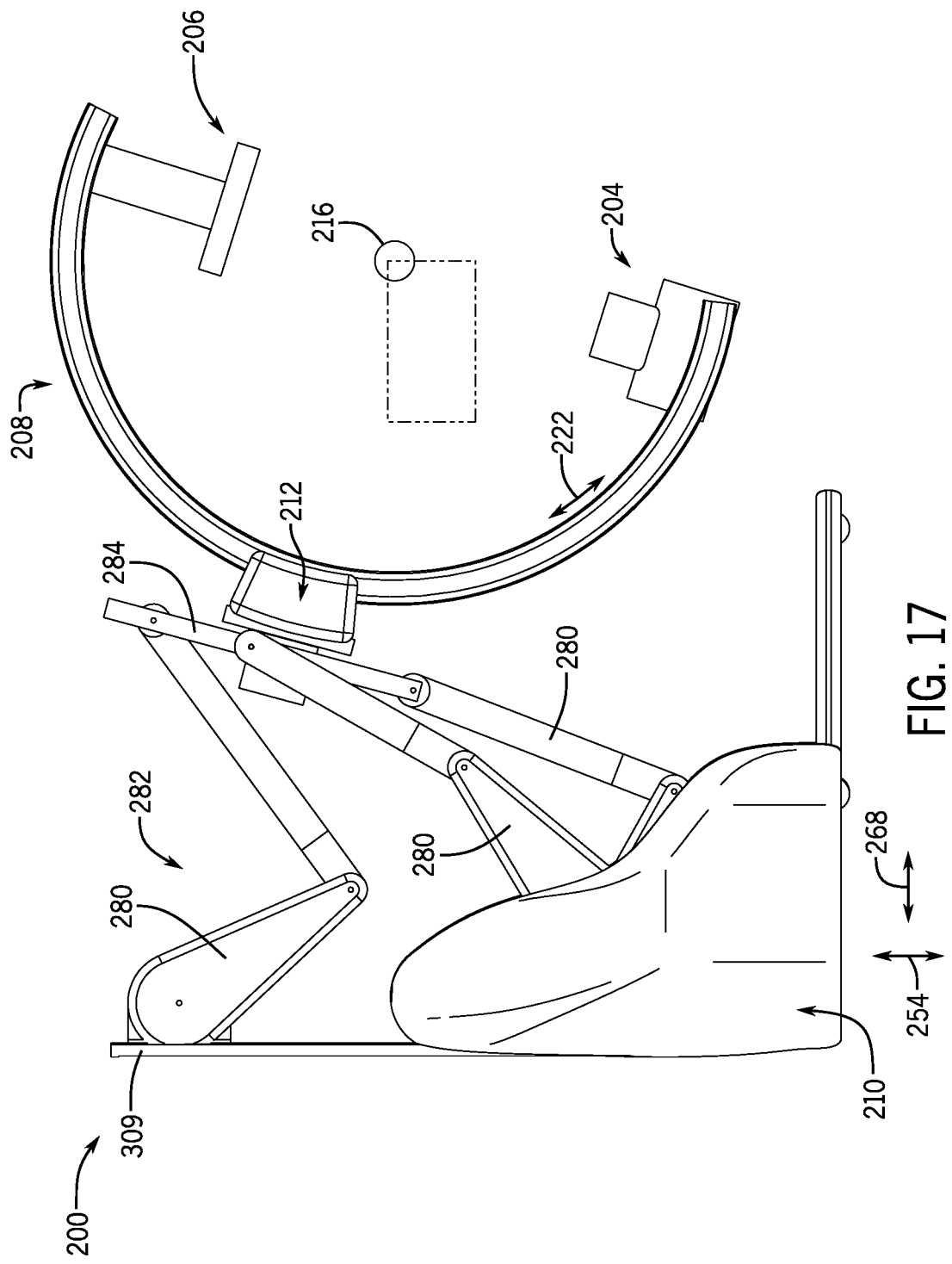
Figure 18:
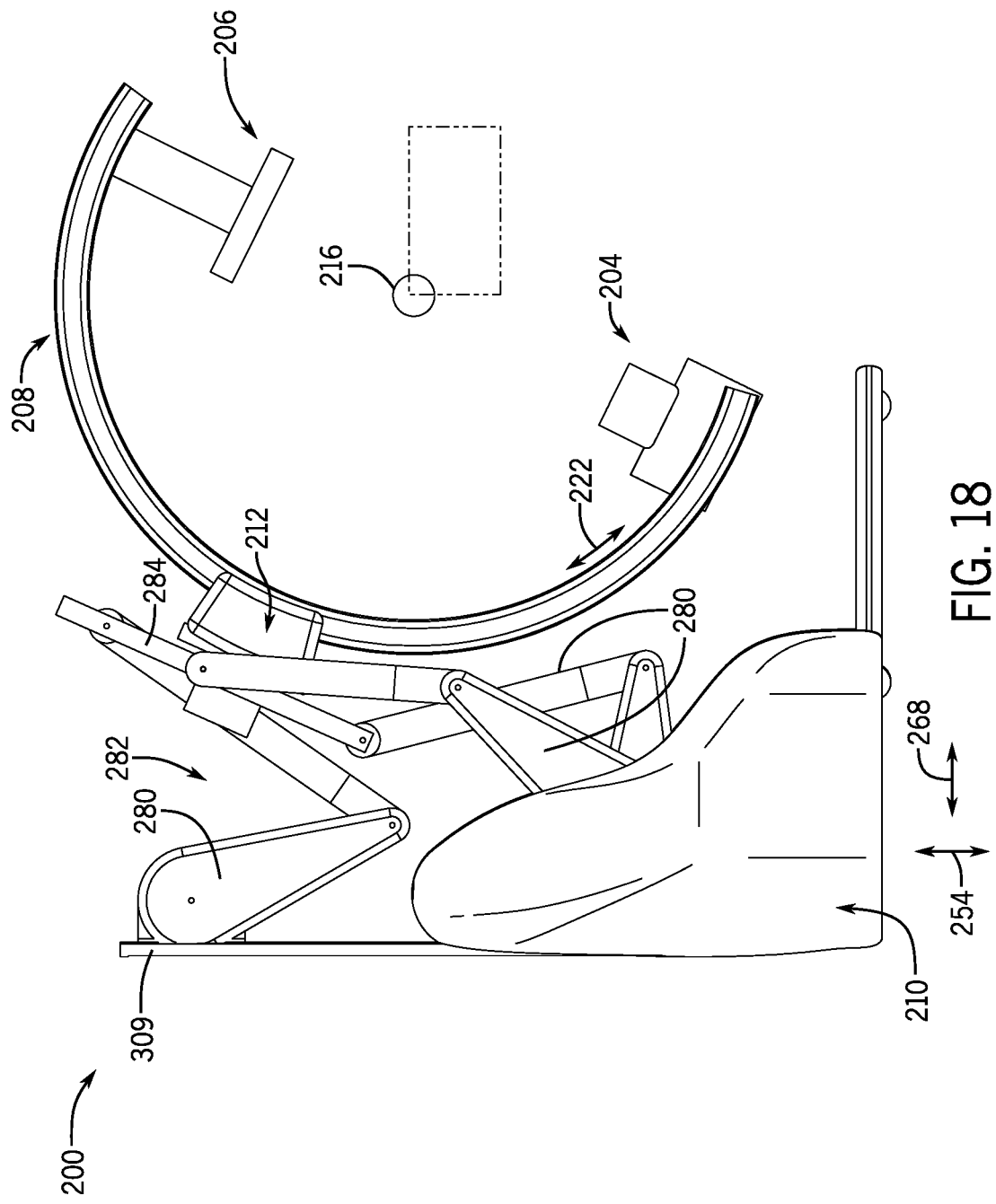
Figure 19:
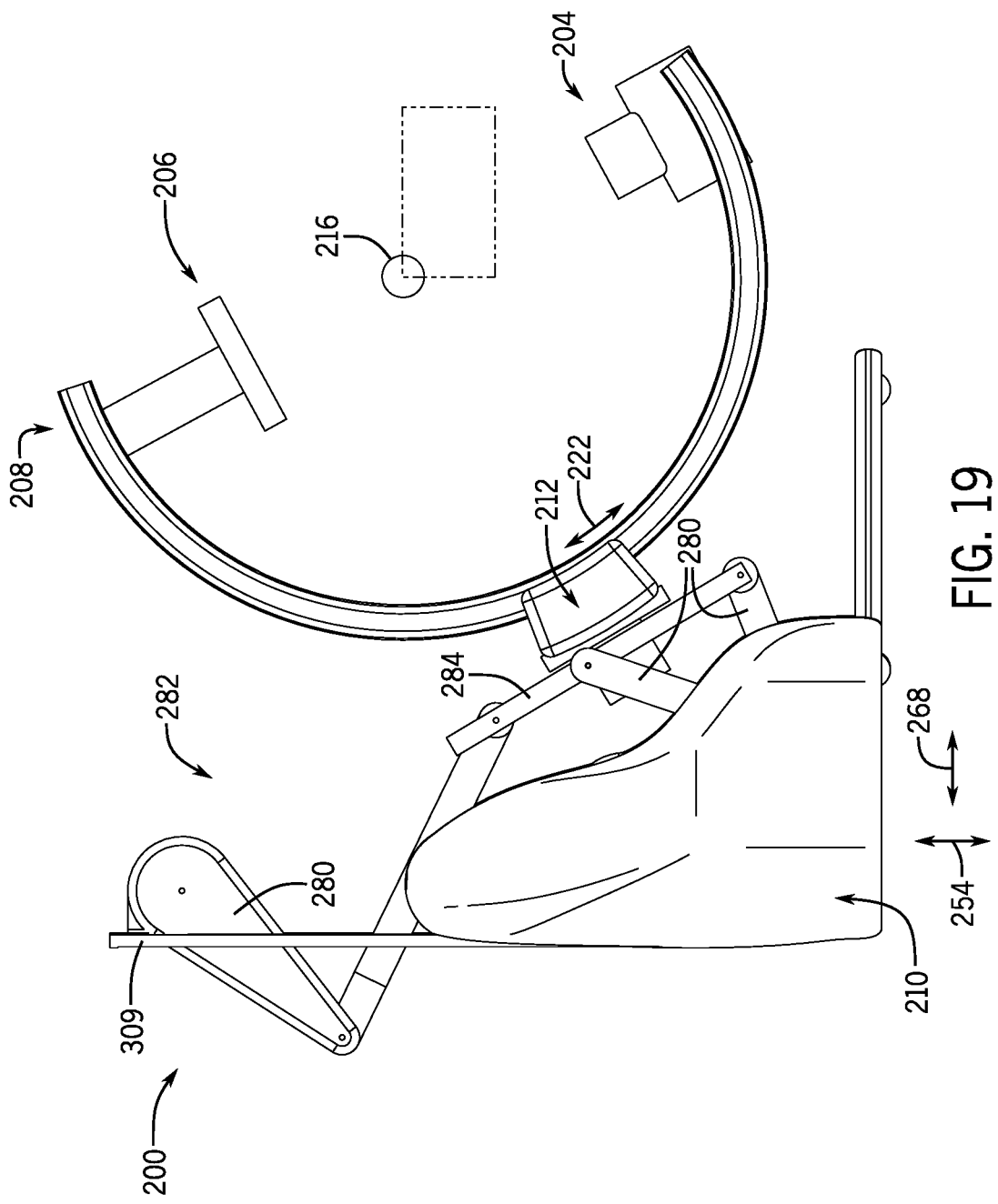
Figure 20:
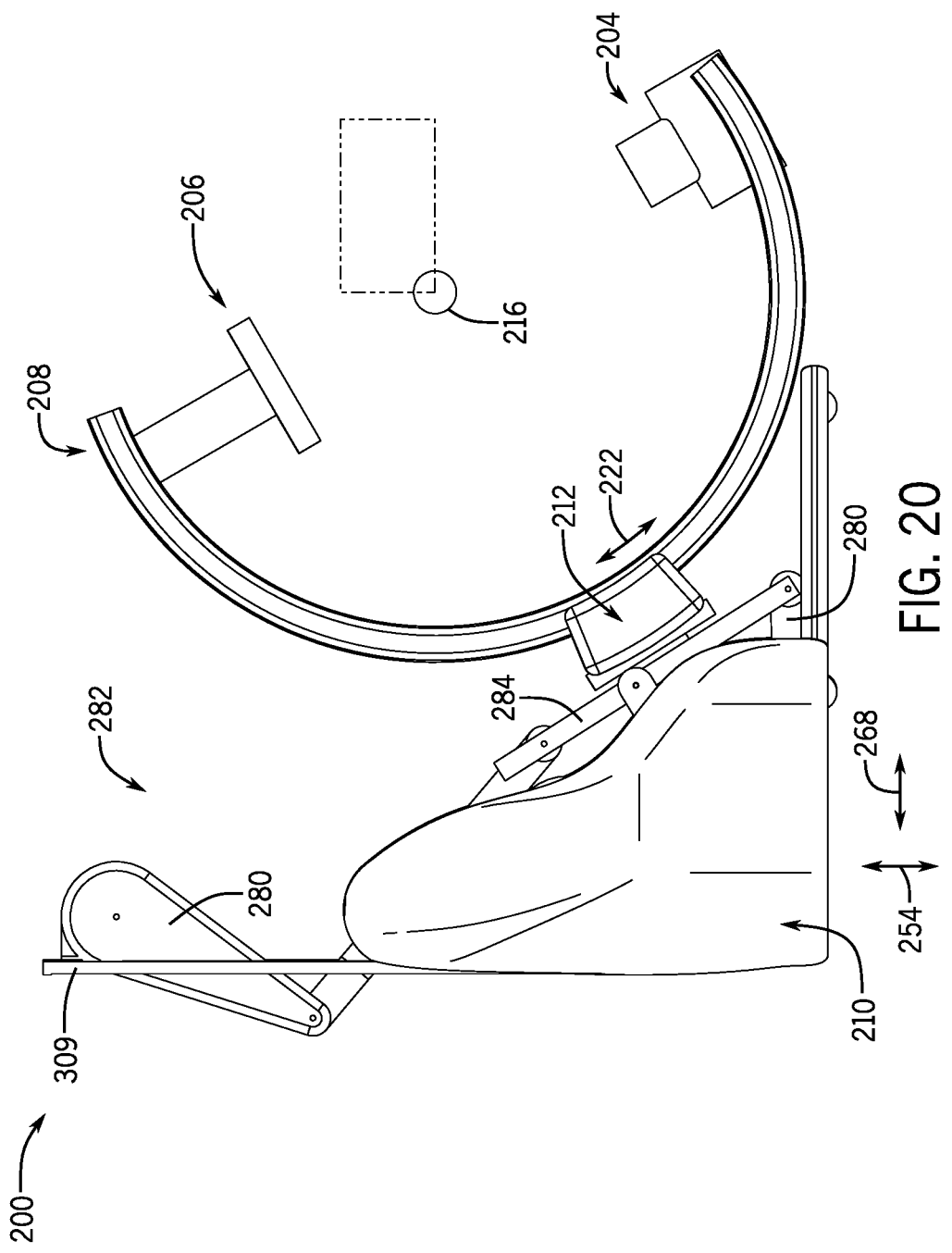

FIGS. 12-20 illustrate movement of the C-arm gantry 208 of the mobile X-ray imaging system 200 of FIGS. 9 and 10 (except robotic arms 280 are located on different sides) utilizing the parallel robotic structure 282 to translate the isocenter 206 in both the horizontal direction 268 and the vertical direction 254. As depicted in FIGS. 12 and 13, in preparation for shifting or translating the isocenter 216 in the horizontal direction 268, the parallel robotic structure 282 is utilized to rotate the C-arm gantry 208 in the x-y plane (i.e., orbital direction 222) so that the X-ray detector 206 is rotated away from the mobile base 210. As depicted in FIGS. 13 and 14, the parallel robotic structure 282 is utilized to shift the isocenter 216 from left to right in the horizontal direction 268. As depicted in FIGS. 14 and 15, in preparation for shifting the isocenter 216 in the vertical direction 254, the parallel robotic structure 282 is utilized to rotate the C-arm gantry 208 in the x-y plane (i.e., orbital direction 222) so that the X-ray detector 206 is rotated toward the mobile base 210. As depicted in FIGS. 15 and 16, the parallel robotic structure 282 is utilized to shift the isocenter 216 upward in the vertical direction 254. As depicted in FIGS. 16 and 17, in preparation for shifting the isocenter 216 in the horizontal direction 268, the parallel robotic structure 282 is utilized to rotate the C-arm gantry 208 in the x-y plane (i.e., the orbital direction 222) so that the X-ray detector 206 is rotated away from the mobile base 210. As depicted in FIGS. 17 and 18, the parallel robotic structure 282 is utilized to shift the isocenter 216 from right to left in the horizontal direction 268. As depicted in FIGS. 18 and 19, in preparation for shifting the isocenter 216 in the vertical direction 254, the parallel robotic structure 282 is utilized to rotate the C-arm gantry 208 in the x-y plane (i.e., the orbital direction 222) so that the X-ray detector 206 is rotated toward the mobile base 210. As depicted in FIGS. 19 and 20, the parallel robotic structure 282 is utilized to shift the isocenter 216 downward in the vertical direction 254.

Returning to FIG. 9 (for simplicity items not shown in FIG. 10), the mobile base 210 includes a plurality of wheels including driven wheels 270 and free wheels 272. The driven wheels 270 may be driven by one or more motors 274 for moving the mobile base 210 and thus the entire mobile X-ray imaging system 200. In addition to moving the mobile X-ray imaging system 200 along the x-axis (i.e., to the left and right), the motor 274 may drive the driven wheels 270 in the z direction, thus enabling the mobile X-ray imaging system 200 to be re-positioned in any orientation in the x-z plane. As an example, two motors 274 for each of the driven wheels 270 may be provided, wherein one motor 274 includes a traction motor and a second motor 274 includes a direction motor. In other examples, dual wheels (with differential traction motors), omnidirectional wheels, or other types of motorized wheels may be used. The free wheels 272 may not be driven by a motor. Further, as depicted, the driven wheels 270 may be positioned in the front of the mobile base 210 (i.e., on the side of the mobile base 210 closer to the C-arm gantry 208) and thus may be advantageously positioned closer to the center of gravity of the mobile X-ray imaging system 200. In some embodiments, the free wheels 272 may be positioned at the front side of the mobile base 210 on a structure extending towards the C-arm gantry 208. In some examples, all wheels of the mobile X-ray imaging system 200 may be driven wheels 270.

In some examples, the mobile X-ray imaging system 200 may include a high voltage generator 276 housed within a housing 278 of the mobile base 210. Providing the high voltage generator 276 within the mobile base 210 increases the weight of the mobile base 210, thus stabilizing the mobile X-ray imaging system 200. Furthermore, providing the high voltage generator 276 within the mobile base 210 avoids housing the high voltage generator 276 remotely from the mobile X-ray imaging system 200, thereby eliminating long high-voltage cables typically connected to the X-ray source 204 via a tether for providing the X-ray source 204 with high voltages.

Technical effects of the disclosed embodiments include providing an X-ray imaging system (e.g., mobile X-ray imaging system) including a C-arm that is coupled to the X-ray imaging system via a parallel robotic structure (e.g., including multiple robotic arms) that provides extra functionality regarding the positioning of the C-arm. In addition to increasing a range of motion for the C-arm, the parallel robotic structure enables an increased range of motion for achieving a desired isocenter position.

This written description uses examples to disclose the present subject matter, including the best mode, and also to enable any person skilled in the art to practice the present approaches, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising: a C-arm with an X-ray source 15 and an X-ray detector 16 mounted thereon opposite each other; a carrier coupled to the C-arm and configured to rotate the C-arm relative to the carrier; a base; and a plurality of robotic arms, wherein each robotic arm of the plurality of robotic arms directly coupling the carrier to the base and comprises two articulated segments and at least two rotary joints.

2. The system of claim 1, wherein the plurality of robotic arms form a parallel robotic structure.

3. The system of claim 2, comprising motors for moving the parallel robotic structure, and the motors are disposed within the base.

4. The system of claim 1, wherein the base comprises a motorized moving base configured to move the system along a surface.

5. The system of claim 1, wherein the plurality of robotic arms comprises three robotic arms.

6. The system of claim 5, wherein each robotic arm of the plurality of robotic arms comprises three rotary joints.

7. The system of claim 6, wherein each robotic arm of the plurality of robotic arms comprises a first end coupled to the base and a second end coupled to the carrier, and wherein the first end coupled to the base is configured to rotate about a rotary joint.

8. The system of claim 7, wherein the plurality of robotic arms is configured to enable two translations of the C-arm and rotation of the C-arm.

9. The system of claim 8, wherein the plurality of robotic arms is configured to enable translation of an isocenter of the C-arm in a vertical direction and horizontal direction relative to a surface that the system is located on.

10. The system of claim 5, wherein each robotic arm of the plurality of robotic arms comprises two articulated segments, two rotary joints and a prismatic joint.

11. The system of claim 10, wherein each robotic arm of the plurality of robotic arms comprises a first end coupled to the base and a second end coupled to the carrier, and wherein the first end coupled to the base is configured to slide in translation along a vertical guide of the base.

12. The system of 1, wherein the plurality of robotic arms is configured, in conjunction with rotation of the C-arm relative to the carrier, to rotate of the X-ray source and the X-ray detector in a plane of the C-arm greater than 180 degrees.

13. A mobile X-ray imaging system, comprising:
a C-arm with an X-ray source and an X-ray detector mounted thereon opposite each other;
a carrier coupled to the C-arm and configured to rotate the C-arm relative to the carrier;
a base; and
a parallel robotic structure comprising three robotic arms coupling the carrier to the base, wherein each robotic arm of three robotic arms comprises two articulated segments, two rotary joints, and a prismatic joint.

14. The mobile X-ray imaging system of claim 13, wherein each robotic arm of the three robotic arms comprises a first end coupled to the base and a second end coupled to the carrier, and wherein the first end coupled to the base is configured to slide in translation along a vertical guide of the base.

15. The mobile X-ray imaging system of claim 14, wherein the first end of two of the three robotic arms slides along a first vertical guide of the base and the first end of the remaining robotic arm of the three robotic arms slides along a second guide of the belt.

16. The mobile X-ray imaging system of claim 14, wherein the base comprises a plurality of conveyor belts configured to drive translation of the first ends of the three robotic arms.

17. A mobile X-ray imaging system, comprising:
- a C-arm with an X-ray source and an X-ray detector mounted thereon opposite each other;
- a carrier coupled to the C-arm and configured to rotate the C-arm relative to the carrier;
- a base; and
- a parallel robotic structure comprising three robotic arms coupling the carrier to the base, wherein each robotic arm of three robotic arms comprises two articulated segments and three rotary joints.

18. The mobile X-ray imaging system of claim 17, wherein each robotic arm of the three robotic arms comprises a first end coupled to the base and a second end coupled to the carrier, and wherein the first end coupled to the base is configured to rotate about a rotary joint.

19. The mobile X-ray imaging system of claim 18, wherein the three robotic arms are configured to enable two translations of the C-arm and rotation of the C-arm.

20. The mobile X-ray imaging system of claim 19, wherein the three robotic arms are configured to enable translation of an isocenter of the C-arm in a vertical direction and a horizontal direction relative to a surface that the mobile X-ray imaging system is located on.

* * * * *